(12) United States Patent
Ye

(10) Patent No.: US 9,504,674 B2
(45) Date of Patent: Nov. 29, 2016

(54) TRKB AGONISTS AND METHODS OF USE

(71) Applicant: EMORY UNIVERSITY, Atlanta, GA (US)

(72) Inventor: Keqiang Ye, Lilburn, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 14/639,343

(22) Filed: Mar. 5, 2015

(65) Prior Publication Data

US 2015/0174107 A1 Jun. 25, 2015

Related U.S. Application Data

(62) Division of application No. 13/643,769, filed as application No. PCT/US2011/039614 on Jun. 8, 2011, now Pat. No. 9,029,561.

(60) Provisional application No. 61/352,991, filed on Jun. 9, 2010.

(51) Int. Cl.
| | |
|---|---|
| A61K 31/415 | (2006.01) |
| A61K 31/35 | (2006.01) |
| A61K 31/4188 | (2006.01) |
| A61K 31/352 | (2006.01) |
| A61K 31/37 | (2006.01) |
| C07D 311/22 | (2006.01) |
| A61K 45/06 | (2006.01) |

(52) U.S. Cl.
CPC ......... *A61K 31/4188* (2013.01); *A61K 31/352* (2013.01); *A61K 31/37* (2013.01); *A61K 45/06* (2013.01); *C07D 311/22* (2013.01)

(58) Field of Classification Search
USPC ........................................ 514/393, 394, 456
See application file for complete search history.

(56) References Cited

U.S. PATENT DOCUMENTS

| | | |
|---|---|---|
| 2002/0198248 A1 | 12/2002 | Kelly |
| 2003/0125264 A1 | 7/2003 | Malik |
| 2004/0063665 A1 | 4/2004 | Bargiotti |
| 2004/0198750 A1 | 10/2004 | Green et al. |
| 2006/0025337 A1 | 2/2006 | Sinclair |
| 2006/0111435 A1 | 5/2006 | Sinclair et al. |
| 2011/0144196 A1 | 6/2011 | Ye |

FOREIGN PATENT DOCUMENTS

| | | |
|---|---|---|
| WO | 95/05169 | 2/1995 |
| WO | 01/03681 | 1/2001 |
| WO | 2004/037193 | 5/2004 |
| WO | 2006/001665 | 1/2006 |
| WO | 2008/091710 | 7/2008 |
| WO | 2009/003147 | 12/2008 |
| WO | 2010/011836 | 1/2010 |
| WO | 2010/014613 | 2/2010 |

OTHER PUBLICATIONS

Sun et al., Journal of Neuroscience Methods 126 (2003) pp. 35-40.*
Sun et al., Journal of Neuroscience Methods vol. 126, pp. 35-40. Published 2003.*
Anjaneyulu et al. "Antidepressant Activity of Quercetin, a Bioflavonoid in Streptozotocin-Induced Diabetic Mice" J Med Food, 2003; 6(4): 391-395.
Berge et al. "Pharmaceutical Salts" J Pharm Sci., 1977; 66(1): 1-18.
Jang et al. "A Selective TrkB agonist with potent neurotrophic activities by 7,8-dihydroxyflavone" PNAS, 2010; 107(6): 2687-2692.
Kato et al. "Studies of Organo Sulfur Compounds" Bull Chem Soc Japan, 1973; 46(3): 860-863.
Liu et al. "A synthetic 7,8-dihydroxyflavone derivative promotes neurogeneisis and exhibits potent antidepressant effect" J. Med. Chem., 2010; 53: 8274-8286.
Liu et al. "O-Methylated Metabolite of 7,8-Dihydroxyflavone Activates TrkB Receptor and Displays Antidepressant Activity" Pharmacology, 2013; 91(3-4): 185-200.
Extended European Search Report for corresponding EP Application No. 11793086.7, mailed Oct. 30, 2013.

* cited by examiner

Primary Examiner — Craig Ricci
Assistant Examiner — George W Kosturko
(74) Attorney, Agent, or Firm — Emory Patent Group

(57) ABSTRACT

Compounds and methods related to the activation of the TrkB receptor are provided. The methods include administering a 7,8-dihydroxyflavone derivative with modified flavone or heterocyclic ring to a subject in need thereof. Methods and compounds for the treatment of disorders including neurologic disorders, neuropsychiatric disorders, and metabolic disorders (e.g., obesity) are provided.

3 Claims, 20 Drawing Sheets

Compound a
7, 8, 2'-trihydroxyflavone

Compound b
7, 8, 3'-trihydroxyflavone

Compound c
7, 8, 4'-trihydroxyflavone

Compound d
7, 3'-dihydroxyflavone

Compound e
5, 7, 8-trihydroxyflavone

Compound f
3, 7, 8, 2'-tetrahydroxyflavone

Compound g
3, 7-dihydroxyflavone

Compound h
7-hydroxy-4'-methoxyflavone

Compound i
8-hydroxy-7-methoxyflavone

Compound j
3, 5, 7, 8, 3', 4'-hexahydroxyflavone

4'-dimethylamino-8-hydroxy-7-methoxyflavone
4'-DMA-8-H-7M-F

4'-dimethylamino-7,8-dihydroxyflavone
4'-DMA-7,8-DHF

4'-dimethylamino-7,8-dimethoxyflavone
4'-DMA-7,8-DMF

Hippocampus

TRKB AGONISTS AND METHODS OF USE

CROSS REFERENCE TO RELATED APPLICATIONS

This application is a divisional of U.S. application Ser. No. 13/643,769 filed Oct. 26, 2012, allowed, which is 35 USC 371 of International Patent Application PCT/US2011/039614, filed on Jun. 8, 2011, and claims the benefit of priority to U.S. Provisional Application No. 61/352,991, filed Jun. 9, 2010, which applications are hereby incorporated by reference in their entireties.

ACKNOWLEDGEMENT

This invention was made with Government Support under Grant No. R01 NS045627 awarded by the National Institutes Of Health. The Government has certain rights in the invention.

FIELD

This disclosure provides compounds and methods for selective activation of the Brain Derived Neurotrophic Factor (BDNF) receptor, TrkB, useful in neuroprotection or treatment of disorders and conditions regulated in part by BDNF signaling. This includes, but is not limited to, neurologic and neuropsychiatric disorders such as depression, anxiety, and central nervous system injuries, as well as metabolic disorders such as obesity.

BACKGROUND

Neurologic and neuropsychiatric disorders such as depression, anxiety, amyotrophic lateral sclerosis, and central nervous system injuries, to name a few, afflict millions of people every year resulting in a multitude of symptoms including weight change, decreased energy, headaches, digestive problems, chronic pain, paralysis, and in certain instances, death.

One class of growth factors proposed as a treatment for neurologic and neuropsychiatric disorders are neurotrophins, which include brain-derived neurotrophic factor (BDNF). BDNF is believed to have neurotrophic action on various neuronal populations including sensory neurons, motor neurons, dopaminergic neurons of the substantia nigra, and cholinergic neurons of the basal forebrain, which are involved in several neurologic and neuropsychiatric disorders. Preclinical evidence indicates that BDNF might be useful as a therapeutic agent for various neurologic and neuropsychiatric disorders; however, the in vivo instability of such a peptide and its inability to effectively cross the blood brain barrier limits its usefulness.

Because such proposed BDNF therapies have not shown much success in clinical trials, focus has shifted to methods of activating known BDNF targets. One such target is the TrkB receptor tyrosine kinase—also known as BDNF/NT-3 growth factor receptor or neurotrophic tyrosine kinase, receptor, type 2, a protein that in humans is encoded by the NTRK2 gene—which acts as the transmembrane protein receptor responsible for receiving BDNF signals and initiating intracellular signaling cascades that culminate in a cellular response. BDNF binding to TrkB triggers its dimerization through conformational changes and autophosphorylation of tyrosine residues in its intracellular domain, resulting in activation of the three major signaling pathways involving mitogen-activated protein kinase (MAPK), phosphatidylinositol 3-kinase (PI3K) and phospholipase C-g1 (PLC-g1). Inactivation of TrkB receptors in mice mimic behavioral defects observed in mice heterozygous for a mutant BDNF allele, including behavioral defects consistent with depression, as well as severe hyperphagia and obesity. This and other evidence from studies support a model whereby TrkB-mediated activation of the BDNF pathway is required for elevated neurogenesis in the hippocampus, a mechanism likely underlying the efficacy of antidepressant treatments. Thus, molecules capable of activating TrkB are attractive candidates as therapeutics for various neurologic, neuropsychiatric, and metabolic disorders.

The small molecule 7,8-dihydroxyflavone has been identified as being capable of binding and triggering the activation of TrkB receptors. This compound exerts neuroprotective effects on mice when injected intraperitoneally, indicating that 7,8-dihydroxyflavone is capable of traversing the blood brain barrier. Certain compounds are described further in (Jang et al., 2010; PCT Appl. Nos. US2009/051535; US2009/051966). Thus, there exists a need to identify improved dihydroxyflavone analogues that possess TrkB agonizing capabilities for the treatment of neurotrohpin-derived disorders.

SUMMARY

This disclosure relates to 7,8-dihydroxyflavone compounds, derivatives, substituted forms, pharmaceutical compositions, and methods for the treatment of TrkB-associated disorders. Such disorders include neurologic disorders, neuropsychiatric disorders (e.g., anxiety or depression), and metabolic disorders (e.g., obesity). The methods include administering to a subject, diagnosed with, at risk or, or exhibiting symptoms of such disorders or conditions a 7,8-dihydroxflavone derivative as described herein with modified flavone rings.

Compounds are provided that can be used in the methods described herein. These compounds may be of the following Formula I:

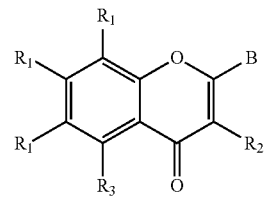

Formula I or a pharmaceutically acceptable salt or prodrug thereof wherein

B is a substituted or unsubstituted $C_3$-$C_{12}$ aryl or substituted or unsubstituted $C_3$-$C_{12}$ heteroaryl;

$R_1$ is independently selected from an OH, or H or wherein two $R_1$ can come together to form an imidazoline ring; $R_2$ is independently selected from a —$OCH_3$, H, or a halogen; and $R_3$ is independently selected from —$OCH_3$, H or a halogen;

with the proviso that when $R_2$ and $R_3$ are both H, then at least two $R_1$ come together to form an imidazoline ring. In certain embodiments, when at least one $R_1$ is an imidazoline ring, $R_2$ is a halogen, and $R_3$ is H. In certain other embodiments, when no $R_1$ is an imidazoline ring, at least one of $R_2$ and $R_3$ is selected from a —$OCH_3$ or a halogen. In certain embodiments, the halogen is F. In certain embodiments, B is a meta, ortho or para substituted aryl or heteroaryl.

In certain specific embodiments, B is independently selected from benzenamine, dimethylbenzenamine, N-bis-(trifluoromethyl)benzenamine, dimethylaniline, or phenylmorpholine.

In certain embodiments, a pharmaceutical composition is provided including a compound of Formula I in a pharmaceutically acceptable carrier. The composition can further include a second active agent, and in particular embodiments will include an anti-anxiolitic agent or an antidepressant.

In certain embodiments, a method is provided for treating or reducing the risk of a TrkB-associated disorder which includes selecting a subject with or at risk of developing a Trk-B associated disorder, and administering to the subject a 7,8-dihydroxflavone derivative as described herein. TrkB-associated disorder can include depression, anxiety, or obesity and the subject can be at risk of or have been diagnosed with depression, anxiety, or obesity. The compound can be administered in a pharmaceutically effective amount for treatment or prevention of a Trkb-associated disorder. A further method of promoting neuroprotection in a subject is provided, which includes selecting a subject in need of neuroprotection, and administering to the subject a 7,8-dihydroxflavone derivative as described herein. A method of activating a TrkB receptor on an isolated neuron also is provided. The method includes providing a neuron with a TrkB receptor, then contacting the TrkB receptor in vitro with a 7,8-dihydroxflavone derivative as described herein in an amount sufficient to activate the TrkB receptor. The neuron can be, for example, a mammalian cell.

In certain embodiments, the disclosure relates to pharmaceutical compositions comprising a pharmaceutically acceptable excipient and compound of Formula A,

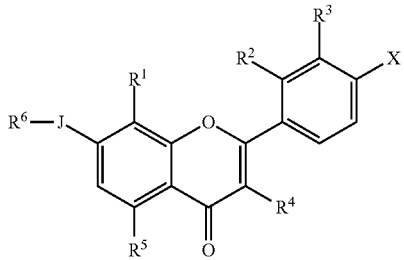

Formula A or salts or prodrugs thereof wherein,

J is O, S, or $NR^7$;

X is hydrogen, dialkylamino, or heterocyclyl, wherein X is optionally substituted with one or more, the same or different $R^8$;

$R^1$ is hydrogen, alkoxy, hydroxy, alkanoyloxy, or amino, wherein $R^1$ is optionally substituted with one or more, the same or different $R^8$; or $R^1$ and $R^6$ and the attached atoms form a heterocyclyl optionally substituted with one or more, the same or different $R^8$;

$R^2$ is hydrogen, alkoxy, hydroxy, or alkanoyloxy, wherein $R^2$ is optionally substituted with one or more, the same or different $R^8$;

$R^3$ is hydrogen, alkoxy, hydroxy, dialkylamino, or alkanoyloxy, wherein $R^3$ is optionally substituted with one or more, the same or different $R^8$;

$R^4$ is hydrogen or halogen;

$R^5$ is hydrogen, alkoxy, hydroxy, or alkanoyloxy wherein $R^5$ is optionally substituted with one or more, the same or different $R^8$; and $R^6$ is hydrogen, alkyl, or alkanoyl wherein $R^6$ is optionally substituted with one or more, the same or different $R^8$;

$R^7$ is hydrogen, alkyl, or alkanoyl wherein $R^7$ is optionally substituted with one or more, the same or different $R^8$;

$R^8$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^8$ is optionally substituted with one or more, the same or different, $R^9$;

$R^9$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl; and provided that if $R^1$ is hydroxy, then $R^2$, $R^3$, $R^4$, and $R^5$ are not all hydrogen.

In certain embodiments, X is hydrogen, dialkylamino, or heterocyclyl; $R^1$ is hydrogen, alkoxy, hydroxy, or alkanoyloxy; $R^2$ is hydrogen, alkoxy, hydroxy, or alkanoyloxy; $R^3$ is hydrogen, alkoxy, hydroxy, alkanoyloxy, dialkylamino, or heterocyclyl; $R^4$ is hydrogen or halogen, $R^5$ is hydrogen, halogen, alkoxy, hydroxy, or alkanoyloxy; and $R^6$ is hydrogen, alkyl, or alkanoyl. In typical embodiments, if $R^1$ is hydroxy, then $R^2$, $R^3$, $R^4$, and $R^5$ are not all hydrogen.

In certain embodiments, $R^1$ and $R^6$ form a five-membered heterocyclic ring such as imidazole.

Typical examples include 7,8,2'-trihydroxyflavone, 7,8,3'-trihydroxyflavone, 7,3'-dihydroxyflavone, 5,7,8-trihydroxyflavone, 3,7-dihydroxyflavone, and 3,7,8,2'-tetrahydroxyflavone, 2-(3-(dimethylamino)phenyl)-7,8-dihydroxy-4H-chromen-4-one, 2-(4-(bis(trifluoromethyl)amino)phenyl)-7,8-dihydroxy-4H-chromen-4-one, 5-fluoro-7,8-dihydroxy-2-phenyl-4H-chromen-4-one, 2-(4-(dimethylamino)phenyl)-5-fluoro-7,8-dihydroxy-4H-chromen-4-one, 3-fluoro-7,8-dihydroxy-2-phenyl-4H-chromen-4-one, 2-(4-(dimethylamino)phenyl)-3-fluoro-7,8-dihydroxy-4H-chromen-4-one, 7,8-dihydroxy-3-methoxy-2-phenyl-4H-chromen-4-one, 8-(4-(dimethylamino)phenyl)chromeno[7,8-d]imidazol-6(3H)-one, 8-(4-(dimethylamino)phenyl)-7-fluorochromeno[7,8-d]imidazol-6(3H)-one or salts thereof. In certain embodiments, the disclosure relates to compound disclosed herein comprising one or more substituents.

In certain embodiments, the excipient is a coating, binder, salt, antiadherent, diluent, or filler. In certain embodiments, the composition is in the form of a tablet, capsule, or solution for injection.

In certain embodiments, the pharmaceutical compositions may be formulated to contain a second therapeutic agent, or the pharmaceutical compositions may be administered in combination with a second therapeutic agent.

In certain embodiments, the compounds may be in a substantially pure form such as greater than 80, 85, 90, 95, or 98% by weight compared to impurities. In addition, of the flavones components in a composition, a specific derivative may make up greater than 20, 30, 40, 50, 60, 70, 80, or 90% of the total flavones components by weight or molecular content.

In certain embodiments, the disclosure relates to methods of treating or preventing a TrkB related disease or condition comprising administering the composition disclosed herein, to a subject diagnosed with, exhibiting symptoms of, or at risk of a TrkB related disease or condition, such as a neurological disease or condition. In certain embodiments, the TrkB relates disease or condition is depression, anxiety, amyotrophic later sclerosis, Alzheimer's disease, Huntington's disease, Rett syndrome, epilepsy, Parkinson's disease, dementia, diabetic neuropathy, peripheral neuropathy, and central nervous system injuries.

In certain embodiments, the disclosure relates to the use of compounds disclosed herein in the production of a medicament for the treatment or prevention of a TrkB related disease or condition.

The details of one or more examples of the compounds and methods are set forth in the accompanying drawings and the description below. Other features, objects, and advantages will be apparent from the description and drawings, and from the claims.

DESCRIPTION OF DRAWINGS

FIG. 2C-2 shows data from P-Akt 4734 ELISA in drug treated mouse brain was analyzed (***, $P<0.001$ vs control; one-way ANOVA: a, $P<0.05$; c, $P<0.001$ vs 7,8-DHF at same concentration, Student's t test). The data were from two sets of replicated experiments.

DETAILED DESCRIPTION

Figure 1A:
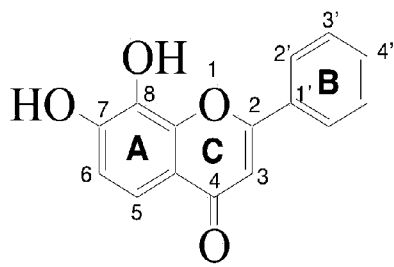
FIG. 1A illustrates the 7,8-Dihydroxyflavone chemical structure with every position in each ring labeled.

Described herein are compounds and methods for the activation of the TrkB receptor. These compounds and methods are effective in the treatment of disorders associated with activation of the TrkB receptor including neurological disorders, neuropsychiatric disorders, and metabolic disorders. Specifically, provided herein, are 7,8-dihydroxyflavone derivatives with modified flavone rings and pharmaceutically acceptable salts, prodrugs, and derivatives thereof. Methods of their use in the treatment of neurologic disorders, neuropsychiatric disorders, and obesity are also described herein.

1. Definitions

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

It is also to be understood that the terminology used herein is for the purpose of describing particular embodiments only, and is not intended to be limiting, since the scope of the present disclosure will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Embodiments of the present disclosure will employ, unless otherwise indicated, techniques of synthetic organic chemistry, biochemistry, biology, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

As used herein a "flavone" refers to any compound comprising a 2-phenyl-4H-chromen-4-one ring system.

The term "TrkB agonist" means a compound, pharmaceutically acceptable salt, prodrug, or derivative thereof that activates the intracellular activity of TrkB, activates the BDNF intracellular signal transduction pathway, upregulates expression or availability of TrkB, or upregulates expression or availability of genes regulated by TrkB-mediated BDNF signalling in a cell or organism.

The term "TrkB-associated disorder" refers to a disorder that is caused or exacerbated by a decrease in BDNF signaling, or any other intracellular signaling cascade that is activated through TrkB.

The term "neuroprotective" or "neuroprotective effect" means that apoptosis of neurons or tissue derived from the nervous system is reduced relative to untreated cells. The TrkB agonists disclosed herein are capable of reducing cell death in neurons relative to untreated controls.

The term "anti-anxiolitic agent" or "antidepressant" refers to a psychiatric medication used to alleviate mood disorders, such as major depression and dysthymia. Examples of antidepressant drugs include, but are not limited to, monoamine oxidase inhibitors (MAOIs), tricyclic antidepressants (TCAs), tetracyclic antidepressants (TeCAs), selective serotonin reuptake inhibitors (SSRIs), and serotonin-norepinephrine reuptake inhibitors (SNRIs).

The term "overweight" or "obesity" refers to a medical condition in which excess body fat has accumulated to the extent that it may have an adverse effect on health, leading to reduced life expectancy and/or increased health problems. Body mass index (BMI), a measurement which compares weight and height, defines people as overweight (pre-obese) when their BMI is between 25 $kg/m^2$ and 30 $kg/m^2$, and obese when it is greater than 30 $kg/m^2$.

The term "organism", "host" or "subject" (as in the subject of the treatment) refers to any living entity comprised of at least one cell. A living organism can be as simple as, for example, a single eukaryotic cell or as complex as a mammal, including a human being. Mammals include, for example, humans; non-human primates such as apes and monkeys; cattle; horses; sheep; rats; mice; pigs; and goats. Non-mammals include, for example, fish and birds.

The terms "treating" and "treatment" refer to causing a therapeutically beneficial effect, such as ameliorating existing symptoms, preventing additional symptoms, ameliorating or preventing the underlying causes of symptoms, postponing or preventing the further development of a disorder and/or reducing the severity of symptoms that will or are expected to develop.

The phrase "a method of treating" or its equivalent refers to a procedure or course of action that is designed to activate the BDNF intracellular signaling cascade in a cell in vitro or within an animal. These methods can be used to treat any disorder that is regulated by BDNF signaling or any disorder where activation of BDNF signaling is thought to provide a beneficial effect. For example, when treating depression, "a method of treating" or its equivalent would refer to a procedure or course of action that is designed to stimulate neurogenesis, or inhibit apoptosis of neurons, or both, in an animal, or to otherwise alleviate the symptoms of depression.

The term "therapeutically effective agent" means a composition that will elicit the biological or medical response of a tissue, system, animal, or human that is being sought by the researcher, veterinarian, medical doctor or other clinician.

The term "therapeutically effective amount" or "effective amount" means the amount of the subject compound or combination that will elicit the biological or medical response of a tissue, system, animal or human that is being sought by the researcher, veterinarian, medical doctor or other clinician.

As used herein, the term "derivative" refers to a chemically or biologically modified version of a chemical compound that is structurally similar to a parent compound and (actually or theoretically) derivable from that parent compound. A "derivative" differs from an "analogue" in that a parent compound may be the starting material to generate a "derivative," whereas the parent compound may not necessarily be used as the starting material to generate an "analogue." A derivative may or may not have different chemical or physical properties of the parent compound. For example, the derivative may be more hydrophilic or it may have altered reactivity as compared to the parent compound. Derivatization (i.e., modification) may involve substitution of one or more moieties within the molecule (e.g., a change in functional group). The term "derivative" also includes conjugates, and prodrugs of a parent compound (i.e., chemically modified derivatives which can be converted into the original compound under physiological conditions).

The term "modulating" as used herein means changing, adjusting, or varying a property of a molecule or pathway including increasing, decreasing, inhibiting, or activating the activity or quantity of the molecule, or activity or inhibition of a pathway.

A "pharmaceutical composition" refers to a mixture of one or more of the compounds described herein, or pharmaceutically acceptable salts thereof, with other chemical components, such as physiologically acceptable carriers and excipients in the form of pills, tablets, capsules, or liquid formulations for injection by needle or similar apparatus. One purpose of a pharmaceutical composition is to facilitate administration of a compound to an organism. It is not intended to be limited to those compositions approved by a regulatory agency and intended to encompass nutritional supplements and other formulations.

As used herein, a "pharmaceutically acceptable carrier" refers to a carrier or diluent that does not cause significant irritation to an organism and does not abrogate the biological activity and properties of the administered compound.

An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

As used herein, the term "topically active agents" refers to compositions of the present disclosure that elicit pharmacological responses at the site of application (contact in a topical application) to a host.

As used herein, the term "topically" refers to application of the compositions of the present disclosure to the surface of the skin and mucosal cells and tissues.

The terms "ar" or "aryl" refer to aromatic homocyclic (i.e., hydrocarbon) mono-, bi- or tricyclic ring-containing groups preferably having 6 to 12 members such as phenyl, naphthyl and biphenyl. Phenyl is a preferred aryl group. The term "substituted aryl" refers to aryl groups substituted with one or more groups, preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, and, the like, where optionally one or more pair of substituents together with the atoms to which they are bonded form a 3 to 7 member ring.

The terms "cycloalkyl" and "cycloalkenyl" refer to mono-, bi-, or tri homocyclic ring groups of 3 to 15 carbon atoms which are, respectively, fully saturated and partially unsaturated. The term "cycloalkenyl" includes bi- and tricyclic ring systems that are not aromatic as a whole, but contain aromatic portions (e.g., fluorene, tetrahydronapthalene, dihydroindene, and the like). The rings of multi-ring cycloalkyl groups may be either fused, bridged and/or joined through one or more spiro unions. The terms "substituted cycloalkyl" and "substituted cycloalkenyl" refer, respectively, to cycloalkyl and cycloalkenyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, and the like. The terms "carbocyclo", "carbocyclic" or "carbocyclic group" refer to both cycloalkyl and cycloalkenyl groups. The terms "substituted carbocyclo", "substituted carbocyclic" or "substituted carbocyclic group" refer to carbocyclo or carbocyclic groups substituted with one or more groups as described in the definition of cycloalkyl and cycloalkenyl.

The terms "halogen" and "halo" refer to fluorine, chlorine, bromine, and iodine.

The terms "heterocycle", "heterocyclic", "heterocyclic group" or "heterocyclo" or "heterocyclyl" refer to fully saturated or partially or completely unsaturated ("heteroaryl") cyclic groups (for example, 3 to 13 member monocyclic, 7 to 17 member bicyclic, or 10 to 20 member tricyclic ring systems, preferably containing a total of 3 to 10 ring atoms) that have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be either fused, bridged and/or joined through one or more spiro unions.

The terms "substituted heterocycle", "substituted heterocyclic", "substituted heterocyclic group" and "substituted heterocyclo" refer to heterocycle, heterocyclic and heterocyclo groups substituted with one or more groups preferably selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, etc., where optionally one or more pair of substituents together with the atoms to which they are bonded form a 3 to 7 member ring.

The term "alkanoyl" refers to alkyl group (which may be optionally substituted as described above) linked to a carbonyl group (e.g., —C(O)-alkyl). Similarly the term, ""alkanoyloxy" refers to a alkanoyl group linked through an oxygen (e.g., —OC(O)-alkyl). Similarly, the term "aroyl" refers to an aryl group (which may be optionally substituted as described above) linked to a carbonyl group (e.g., —C(O)-aryl).

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include, and are contemplated to include, halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NR$_a$R$_b$, —NR$_a$C(=O)R$_b$, —NR$_a$C(=O)NR$_a$NR$_b$, —NR$_a$C(=O)OR$_b$, —NR$_a$SO$_2$R$_b$, —C(=O)R$_a$, —C(=O)OR$_a$, —C(=O)NR$_a$R$_b$, —OC(=O)NR$_a$R$_b$, —OR$_a$, —SR$_a$, —SOR$_a$, —S(=O)$_2$R$_a$, —OS(=O)$_2$R$_a$ and —S(=O)$_2$OR$_a$. R$_a$ and R$_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

Throughout the specification, groups and substituents thereof may be chosen to provide stable moieties and compounds.

The disclosed compounds form salts which are also within the scope of this invention. Reference to a compound of any of the formulas herein is understood to include reference to salts thereof, unless otherwise indicated. The term "salt(s)", as employed herein, denotes acidic and/or basic salts formed with inorganic and/or organic acids and bases. In addition, when a compound contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation.

The disclosed compounds that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those Tormea with sulfuric acid), sulfonates (such as those mentioned herein), tartrates, thiocyanates, toluenesulfonates such as tosylates, undecanoates, and the like.

The disclosed compounds that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Solvates of the compounds of the disclosure are also contemplated herein. Solvates of the compounds are preferably hydrates.

To the extent that the disclosed compounds, and salts thereof, may exist in their tautomeric form, all such tautomeric forms are contemplated herein as part of the present disclosure.

All stereoisomers of the present compounds, such as those which may exist due to asymmetric carbons on the various substituents, including enantiomeric forms (which may exist even in the absence of asymmetric carbons) and diastereomeric forms, are contemplated within the scope of this disclosure. Individual stereoisomers of the compounds of the disclosure may, for example, be substantially free of other isomers, or may be admixed, for example, as racemates or with all other, or other selected, stereoisomers. The chiral centers of the compounds of the present disclosure can have the S or R configuration as defined by the IUPAC 1974 Recommendations.

The terms "including", "such as", "for example" and the like are intended to refer to exemplary embodiments and not to limit the scope of the present disclosure.

2. Compositions of Matter 7,8-dihydroxflavone derivatives with modified flavone or heterocycle rings useful with the methods described herein include compounds represented by Formula I:

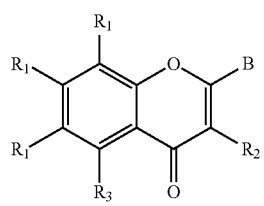

Formula I and pharmaceutically acceptable salts and prodrugs thereof, wherein

B is a substituted or unsubstituted $C_3$-$C_{12}$ aryl or substituted or unsubstituted $C_3$-$C_{12}$ heteroaryl;

$R_1$ is independently selected from an OH, or H or wherein two $R_1$ can come together to form an imidazoline ring;

$R_2$ is independently selected from a —OCH$_3$, H, or a halogen; and $R_3$ is independently selected from —OCH$_3$, H or a halogen;

with the proviso that when $R_2$ and $R_3$ are both H, then at least two $R_1$ come together to form an imidazoline ring. In certain embodiments, when at least one $R_1$ is an imidazoline ring, $R_2$ is a halogen, and $R_3$ is H. In certain other embodiments, when no $R_1$ is an imidazoline ring, at least one of $R_2$ and $R_3$ is selected from a —OCH$_3$ or a halogen. In certain embodiments, the halogen is F. In certain embodiments, B is a meta, ortho or para substituted aryl or heteroaryl. In certain specific embodiments, B is independently selected from benzenamine, dimethylbenzenamine, N-bis-(trifluoromethyl)benzenamine, dimethylaniline, or phenylmorpholine.

In certain embodiments, $R_1$ is a —OH. In certain other embodiments, $R_1$ is —H. In certain other embodiments, two $R_1$ can come together to form an imidazoline ring.

In certain embodiments, $R_2$ is a halogen. In certain other embodiments, $R_2$ is —OCH$_3$. In certain other embodiments, $R_2$ is hydrogen.

In certain embodiments, $R_3$ is a halogen. In certain other embodiments, $R_3$ is —OCH$_3$. In certain other embodiments, $R_3$ is hydrogen.

In certain embodiments, B is a benzenamine. In certain other embodiments, B is a dimethylbenzenamine. In certain other embodiments, B is N-bis-(trifluoromethyl)benzenamine. In certain other embodiments, B is a dimethylaniline. In certain other embodiments, B is a phenylmorpholine.

The compounds represented by Formula I include derivatives of 7,8-dihydroxyflavone with modified flavone rings that are more soluble than 7,8-dihydroxyflavone and retain the ability to activate the TrkB receptor. The effectiveness of various 7,8-dihydroxyflavone derivatives relative to 7,8-dihydroxyflavone with respect to activating the TrkB receptor may vary. However, without wishing to be bound by theory, even if a particular derivative has a lower effectiveness than 7,8-dihydroxyflavone at activating the TrkB receptor, improvements in solubility can increase the overall effectiveness of the derivative as used, e.g., in the methods described herein.

In certain embodiments of Formula I, B is a meta, para, or ortho substituted phenyl or substituted or unsubstituted $C_5$ or $C_6$ heteroaryl. In certain embodiments, B is:

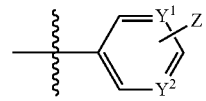

wherein $Y^1$ and $Y^2$ are each independently —O, N, S, or CH$_2$; and Z is halogen, —OR$_4$, —NR$_4$R$_5$, wherein $R_4$ and $R_5$ are each selected from hydrogen, a substituted or unsubstituted $C_{1-12}$ alkyl, substituted or unsubstituted $C_{2-12}$ alkenyl, substituted or unsubstituted $C_{2-12}$ alkynyl, $C_{3-12}$ cycloalkyl, substituted or unsubstituted $C_{3-12}$ heterocycloalkyl, substituted or unsubstituted $C_{3-12}$ cycloalkenyl, substituted or unsubstituted $C_{3-12}$ heterocycloalkenyl, substituted or unsubstituted $C_{3-12}$ cycloalkynyl, or substituted or unsubstituted $C_{3-12}$ heterocycloalkynyl or wherein $R_4$ and $R_5$ can come together with the N to which they are attached to form a 4-8 membered cyclic or heterocyclic ring, which may optionally be substituted with one or more substituents and wherein B can include 0, 1, 2, 3 or 4 Z groups. Examples of Z further include —NH$_2$, —NHCH$_3$, —N(CH$_3$)$_2$, —N(CF$_3$)$_2$,

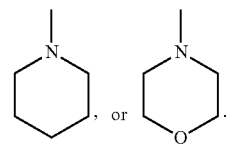

In another embodiement, B is:

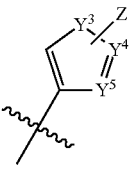

wherein $Y^3$, $Y^4$, and $Y^5$ are each independently —O, N, S, or $CH_2$; and Z is as defined above and wherein B includes 0, 1, 2, 3, or 4 Z groups.

More particular examples of B include:

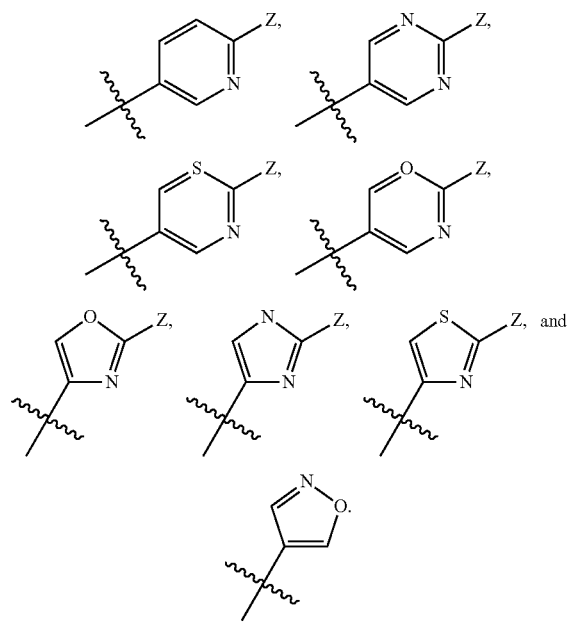

wherein Z is as defined above. In specific embodiments, Z is selected from a halogen or —$NR_4R_5$ wherein $R_4$ and $R_5$ are as defined above. In more specific embodiments, Z is —$NR^4R^5$ wherein $R_4$ and $R_5$ are each selected from substituted or unsubstituted $C_{1-4}$ alkyl. In other embodiments, Z is a halogen. In some specific embodiments, the halogen is F. In other specific embodiments, B is selected from a benzenamine, dimethylbenzenamine, N-bis-(trifluoromethyl)benzenamine, dimethylaniline, and phenylmorpholine.

In certain embodiments, compounds that are TrkB agonists are as follows, wherein each O that does not have two bonds includes an additional H:

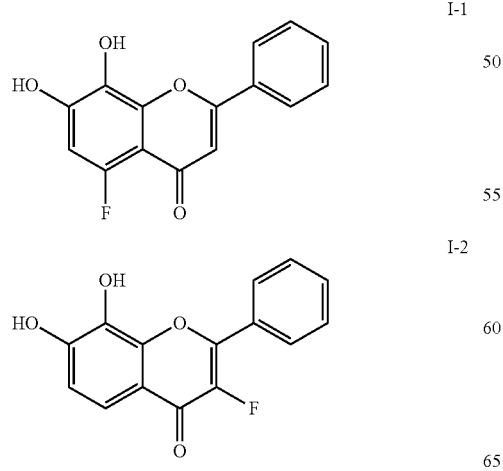

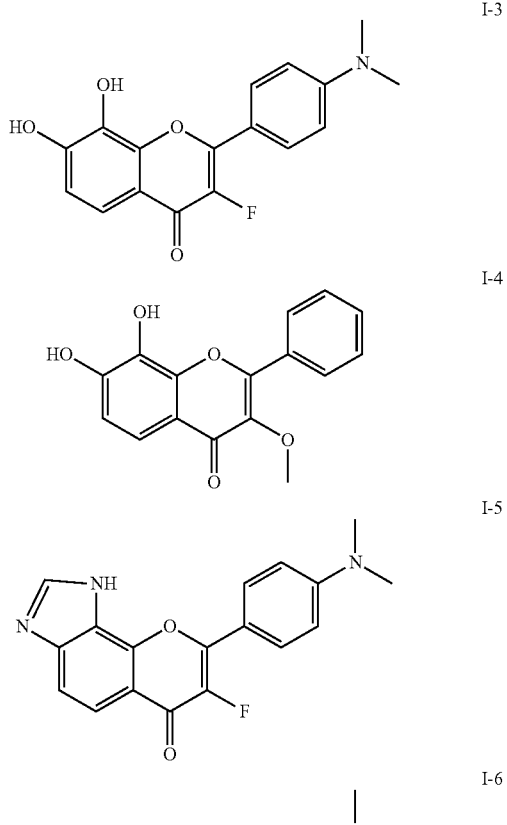

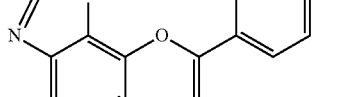

In certain embodiments, the disclosure relates to pharmaceutical compositions comprising a pharmaceutically acceptable excipient and compound of Formula B,

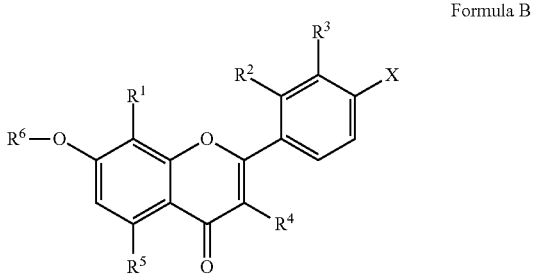

or salts or prodrugs thereof wherein,

X is hydrogen, dialkylamino, or heterocyclyl, wherein X is optionally substituted with one or more, the same or different $R^8$;

$R^1$ is hydrogen, alkoxy, hydroxy, alkanoyloxy, or amino, wherein $R^1$ is optionally substituted with one or more, the same or different $R^8$;

$R^2$ is hydrogen, alkoxy, hydroxy, or alkanoyloxy, wherein $R^2$ is optionally substituted with one or more, the same or different $R^8$;

$R^3$ is hydrogen, alkoxy, hydroxy, dialkylamino, or alkanoyloxy, wherein $R^3$ is optionally substituted with one or more, the same or different $R^8$;

$R^4$ is hydrogen or halogen;

$R^5$ is hydrogen, alkoxy, hydroxy, or alkanoyloxy wherein $R^5$ is optionally substituted with one or more, the same or different $R^8$; and $R^6$ is hydrogen, alkyl, or alkanoyl wherein $R^6$ is optionally substituted with one or more, the same or different $R^8$;

$R^7$ is hydrogen, alkyl, or alkanoyl wherein $R^7$ is optionally substituted with one or more, the same or different $R^8$;

$R^8$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^8$ is optionally substituted with one or more, the same or different, $R^9$;

$R^9$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl; and provided that if $R^1$ is hydroxy, then $R^2$, $R^3$, $R^4$, and $R^5$ are not all hydrogen.

In certain embodiments, the disclosure relates to pharmaceutical compositions comprising a pharmaceutically acceptable excipient and compound of Formula D,

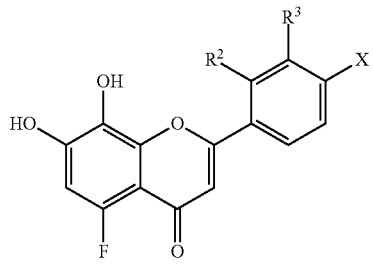

Formula D or salts or prodrugs thereof wherein,

X is hydrogen, dialkylamino, or heterocyclyl, wherein X is optionally substituted with one or more, the same or different $R^8$;

$R^2$ is hydrogen, alkoxy, hydroxy, or alkanoyloxy, wherein $R^2$ is optionally substituted with one or more, the same or different $R^8$;

$R^3$ is hydrogen, alkoxy, hydroxy, dialkylamino, or alkanoyloxy, wherein $R^3$ is optionally substituted with one or more, the same or different $R^8$;

$R^8$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^8$ is optionally substituted with one or more, the same or different, $R^9$;

$R^9$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the disclosure relates to pharmaceutical compositions comprising a pharmaceutically acceptable excipient and compound of Formula E,

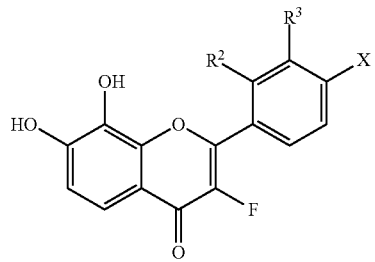

Formula E or salts or prodrugs thereof wherein,

X is hydrogen, dialkylamino, or heterocyclyl, wherein X is optionally substituted with one or more, the same or different $R^8$;

$R^2$ is hydrogen, alkoxy, hydroxy, or alkanoyloxy, wherein $R^2$ is optionally substituted with one or more, the same or different $R^8$;

$R^3$ is hydrogen, alkoxy, hydroxy, dialkylamino, or alkanoyloxy, wherein $R^3$ is optionally substituted with one or more, the same or different $R^8$;

$R^8$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^8$ is optionally substituted with one or more, the same or different, $R^9$;

$R^9$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, X is hydrogen, dialkylamino, or heterocyclyl; $R^1$ is hydrogen, alkoxy, hydroxy, or alkanoyloxy; $R^2$ is hydrogen, alkoxy, hydroxy, or alkanoyloxy; $R^3$ is hydrogen, alkoxy, hydroxy, alkanoyloxy, dialkylamino, or heterocyclyl; $R^4$ is hydrogen or halogen, $R^5$ is hydrogen, halogen, alkoxy, hydroxy, or alkanoyloxy; and $R^6$ is hydrogen, alkyl, or alkanoyl. In typical embodiments, if $R^1$ is hydroxy, then $R^2$, $R^3$, $R^4$, and $R^5$ are not all hydrogen.

In certain embodiments, the disclosure relates to pharmaceutical compositions comprising a pharmaceutically acceptable excipient and compound of Formula F,

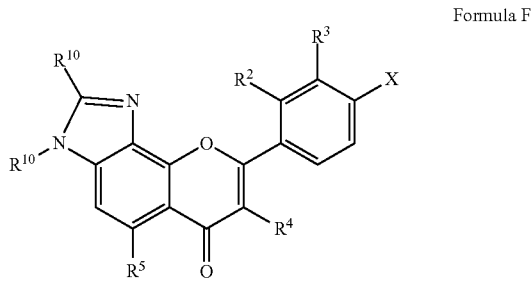

Formula F or salts or prodrugs thereof wherein,

X is hydrogen, dialkylamino, or heterocyclyl, wherein X is optionally substituted with one or more, the same or different $R^8$;

$R^2$ is hydrogen, alkoxy, hydroxy, or alkanoyloxy, wherein $R^2$ is optionally substituted with one or more, the same or different $R^8$;

$R^3$ is hydrogen, alkoxy, hydroxy, dialkylamino, or alkanoyloxy, wherein $R^3$ is optionally substituted with one or more, the same or different $R^8$;

$R^4$ is hydrogen or halogen;

$R^5$ is hydrogen, alkoxy, hydroxy, or alkanoyloxy wherein $R^5$ is optionally substituted with one or more, the same or different $R^8$; and $R^8$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^8$ is optionally substituted with one or more, the same or different, $R^9$;

$R^9$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl; and $R^{10}$ and $R^{11}$ are each, the same or different hydrogen, alkyl, or alkanoyl.

3. Methods of Synthesis

Methods for for the synthesis of 7,8-dihydroxflavone derivatives with modified flavone or heterocycle rings are provided below. According to scheme 1,2,3,4-trihydroxyacetophenone is first treated with $K_2CO_3$ and TBAI under refluxing conditions, followed by an acid-induced dehydrative cyclization to generate the desired unprotected flavones or heterocycles, as depicted below.

Scheme 1

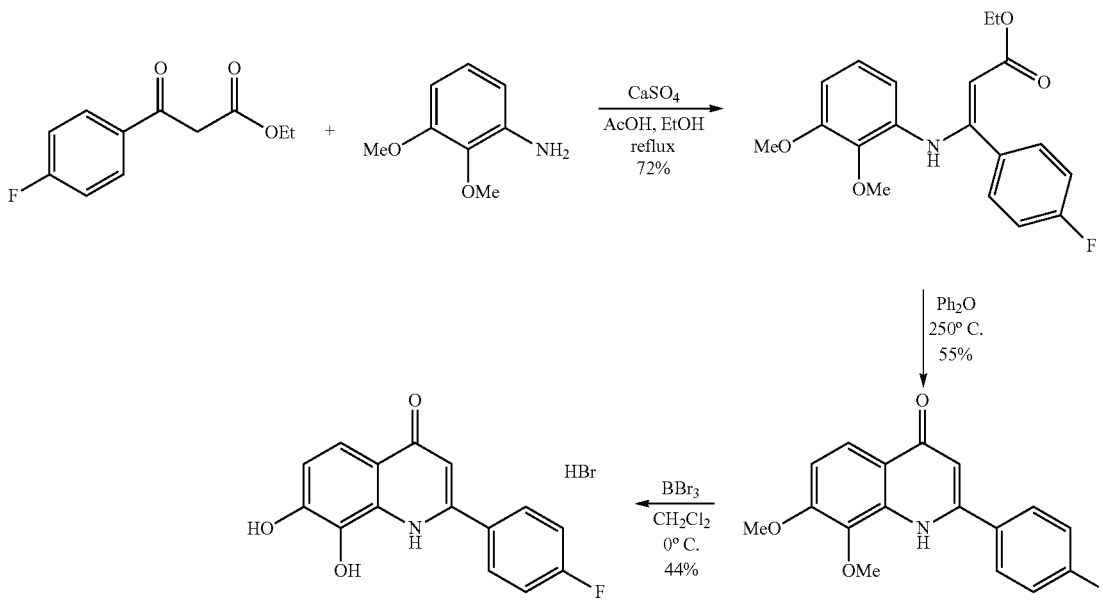

7,8-dihydroxflavone with modified flavone or heterocycle rings can also be prepared by tandem treatment of the diprotected acetophenones with functionalized acid chlorides in pyridine, followed by base treatment, and then acid induced cyclization and deprotection of the aryl ethers, as depicted below.

Scheme 2
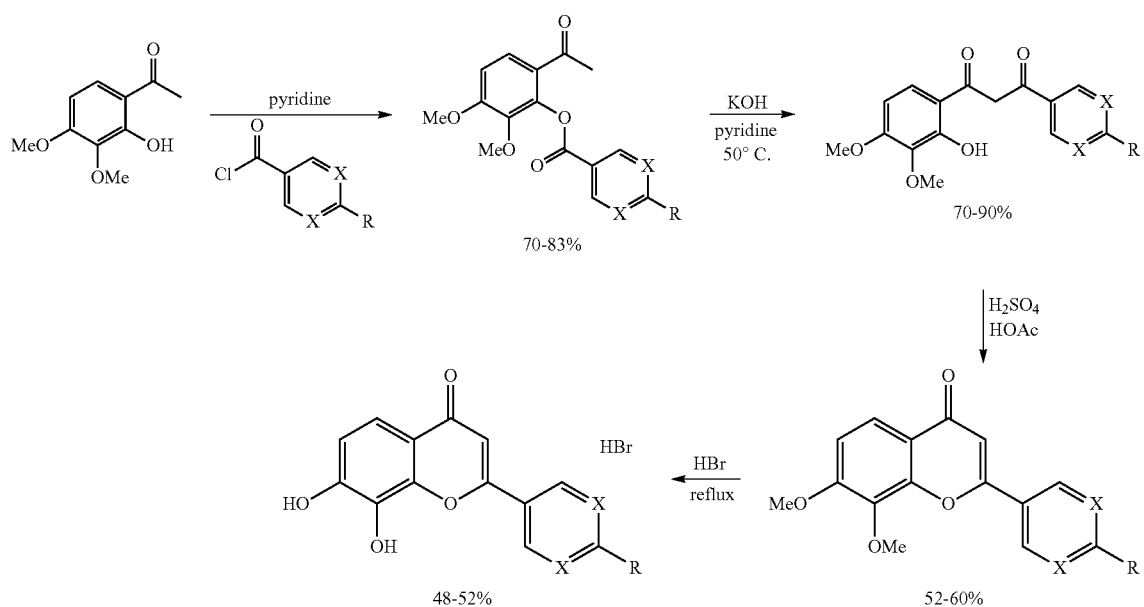
R = NMe₂, X = CH
R = F, X = CH
R = H, X = N
Additional derivative where prepared according to Schemes 3, 4, and 5 below
Scheme 3
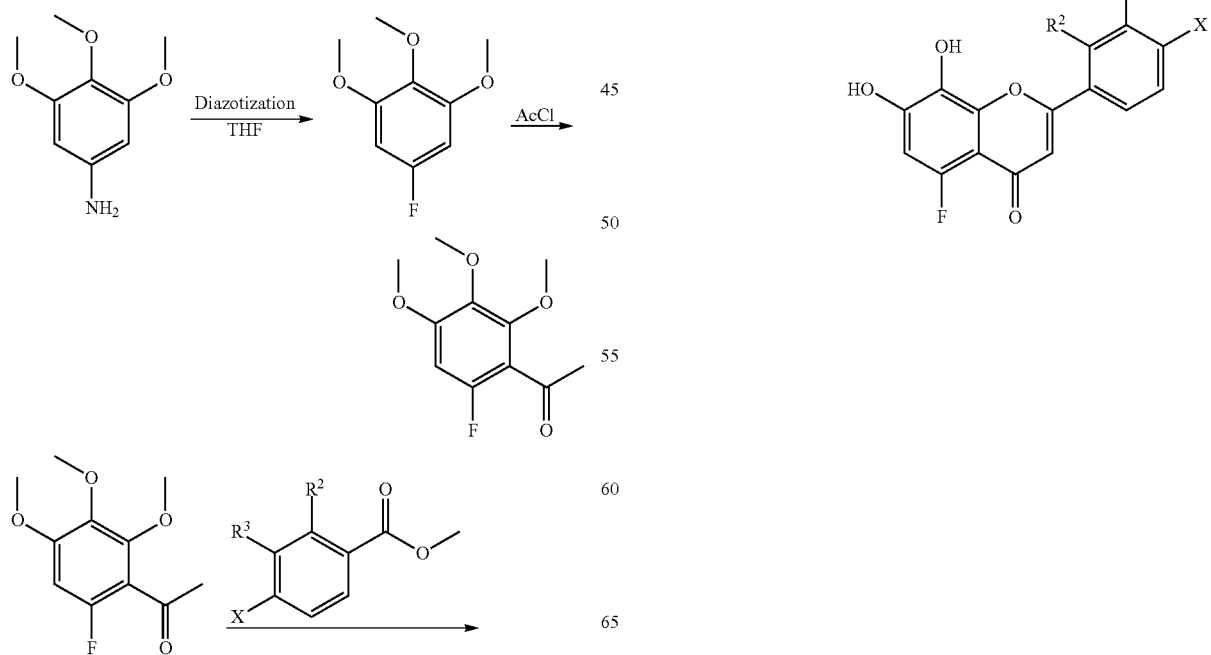
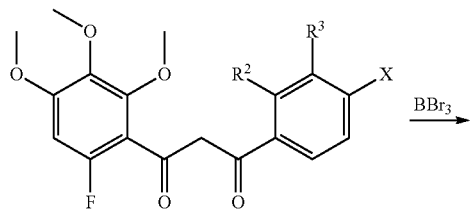

Scheme 4
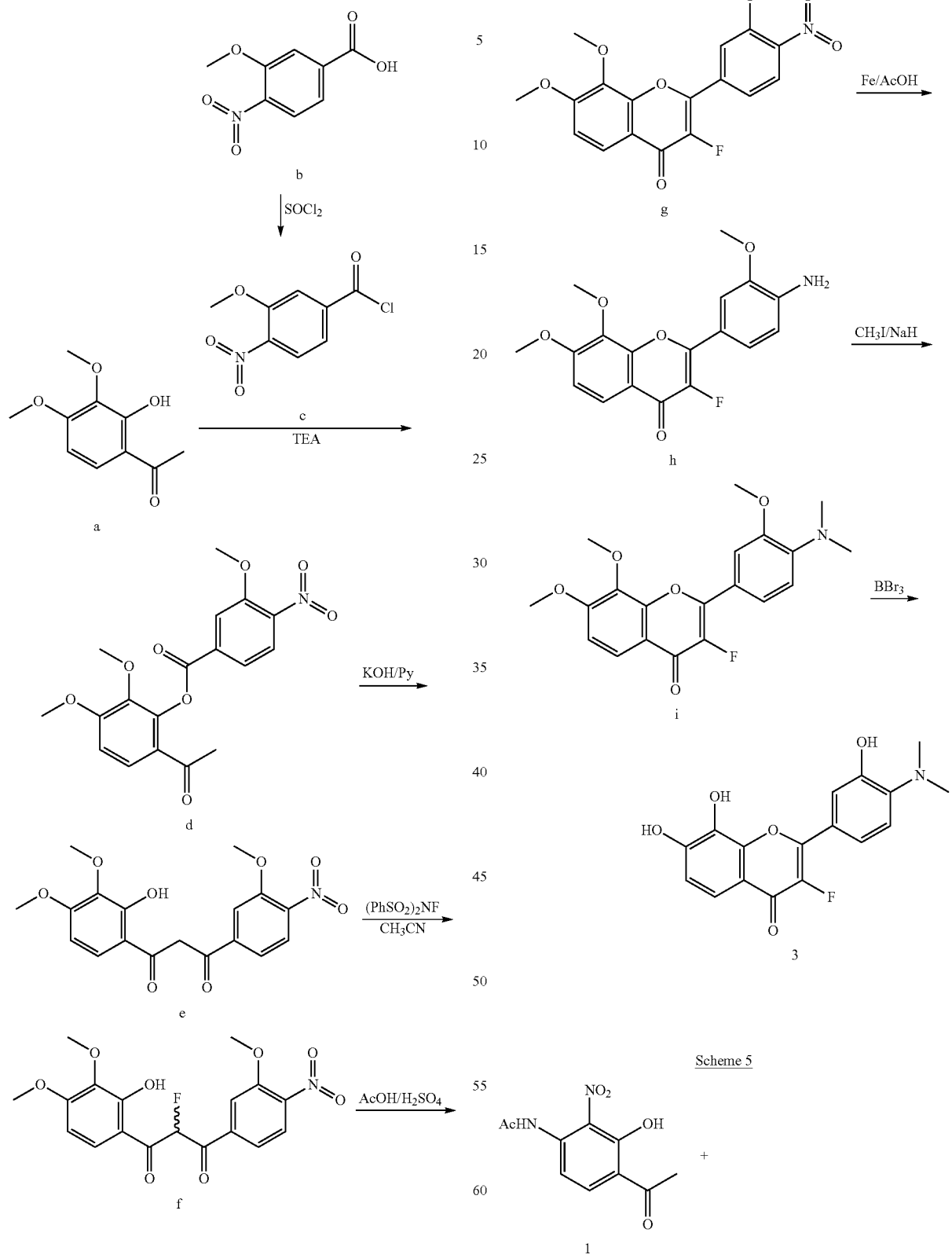
Scheme 5
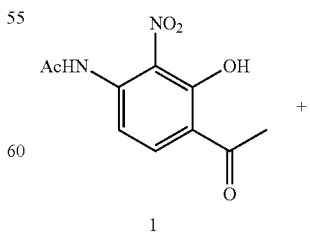

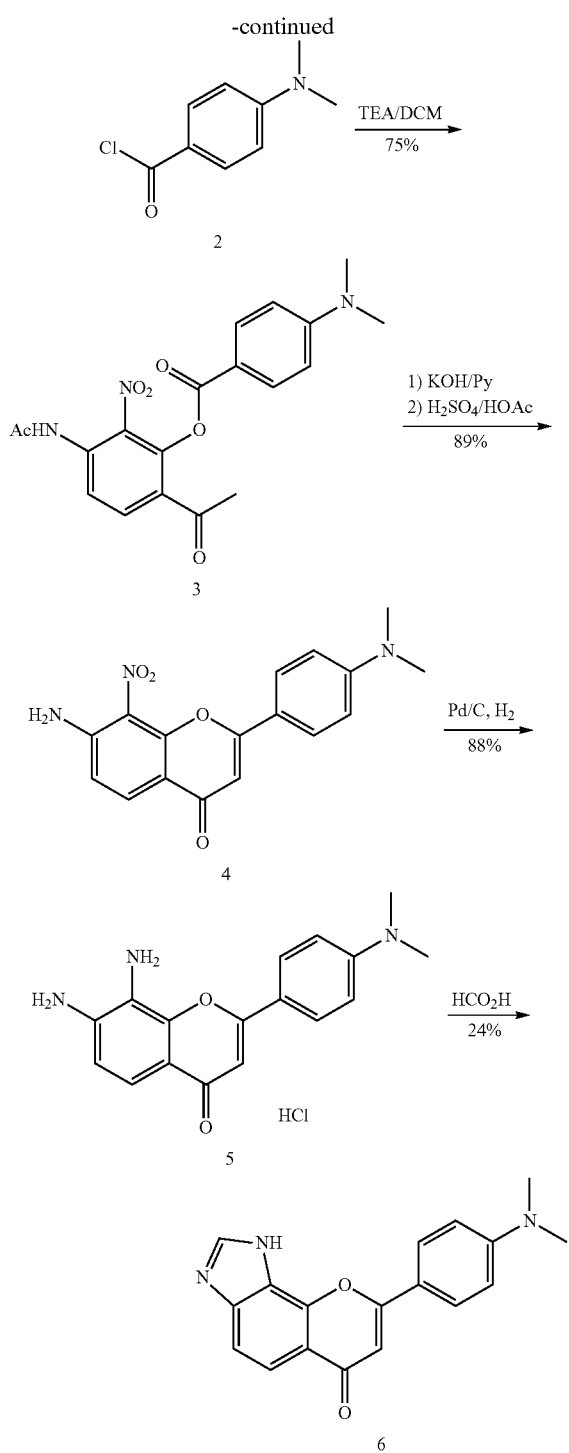

4. Methods of Use

The methods described herein include a method of treating or reducing the risk of disorders associated with activation of the TrkB receptor including neurological disorders, neuropsychiatric disorders, and metabolic disorders in a subject. Examples of neurological and neuropsychiatric disorders include depression, anxiety, Alzheimer's, CNS injuries, and the like. Examples of metabolic disorders include obesity and hyperphagia. This method includes the steps of selecting a subject with or at risk of developing the neurological disorder, neuropsychiatric disorder, or obesity, and administering to the subject a therapeutically effective amount of 7,8-dihydroxyflavone with a modified flavone or heterocycle ring. The 7,8-dihydroxflavone with a modified flavone or heterocycle ring can be administered systemically (e.g., orally, parenterally (e.g. intravenously), intramuscularly, intreperitoneally, transdermally (e.g., by a patch), extracorporeally, topically, by inhalation, subcutaneously or the like), by administration into the central nervous system (e.g., into the brain (intracerebrally or intra ventricularly), spinal cord, or into the cerebrospinal fluid), or any combination thereof.

The subject in need thereof can be a patient diagnosed as suffering from depression or anxiety. These diseases and their diagnoses are very clearly defined in the "Diagnostic and Statistical Manual of Mental Disorders (DSM-IV)" published by the American Psychiatric Association. This manual sets forth diagnostic criteria, descriptions and other information to guide the classification and diagnosis of mental disorders and is commonly used in the field of neuropsychiatry. It is for instance available on the Internet under:

http://www.behavenet.com/capsules/disorders/dsm4tr.htm. In certain embodiments, the patient is being administered an antidepressant or antianxiolytic medication. In certain embodiments, the patient has been diagnosed by a mental health professional (e.g., a psychiatrist) with an anxiety or depression disorder.

The subject in need thereof can be a patient diagnosed as suffering from being overweight or obese. Being overweight and obesity can be diagnosed by health or nutritional professionals (e.g., physicians, nurses, dieticians, and the like) when the patient's body mass index (BMI), a measurement which compares weight and height, is between 25 kg/m$^2$ and 30 kg/m$^2$, and obese when it is greater than 30 kg/m$^2$.

Also provided is a method of promoting neuroprotection in a subject. This method includes the steps of selecting a subject in need of neuroprotection, and administering to the subject a therapeutically effective amount of 7,8-dihydroxyflavone with a modified flavone or heterocycle ring. A subject in need of neuroprotection can, for example, be a subject that has amyotrophic lateral sclerosis (ALS) or a central nervous system injury. A central nervous system injury includes, for example, a brain injury, a spinal cord injury, or a cerebrovascular event (e.g., a stroke). Methods can further comprise testing the effectiveness of 7,8-dihydroxyflavone with a modified flavone or heterocycle ring. Testing the effectiveness can include, but is not limited to, imaging (e.g., Magnetic Resonance Imaging (MRI)) and functional measurements (e.g., survival or clinical symptoms like analysis of speech patterns, logic, comprehension, memory, mood, and orientation). The method optimally further comprises adjusting the dosage or treatment regimen of 7,8-dihydroxyflavone with a modified flavone or heterocycle ring.

Further provided is a method of activating a TrkB receptor on a neuron (e.g., a mammalian neuron). This method includes the steps of providing a neuron with a TrkB receptor, and contacting the TrkB receptor in vitro with a 7,8-dihydroxyflavone with a modified flavone or heterocycle ring in an amount sufficient to activate the TrkB receptor. Also provided is a method of screening for an agent that potentiates the TrkB receptor activation. The screening method includes activating the TrkB receptor on a neuron as described and contacting the neuron with the agent to be screened. An enhanced effect indicates the agent potentiates the effect of 7,8-dihydroxyflavone with a modified flavone or heterocycle ring.

5. Pharmaceutical Compositions

The compounds described herein or derivatives thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the compound described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing the compound described herein or derivatives thereof suitable for parenteral injection may comprise physiologically acceptable sterile aqueous or non-aqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents. Solid compositions of a similar type may also be employed as fillers in soft and hard-filled gelatin capsules using such excipients as lactose or milk sugar as well as high molecular weight poly ethylenegly cols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in microencapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, may contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like. Compositions of the compounds described herein or derivatives thereof for rectal administrations are preferably suppositories, which can be prepared by mixing the compounds with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of the compounds described herein or derivatives thereof include ointments, powders, sprays, and inhalants. The compounds described herein or derivatives thereof are admixed under sterile conditions with a physiologically acceptable carrier and any preservatives, buffers, or propellants as may be required. Ophthalmic formulations, ointments, powders, and solutions are also contemplated as being within the scope of the compositions.

The term pharmaceutically acceptable salt as used herein refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. See S. M. Barge et al., J. Pharm. Sci. (1977) 66, 1, which is incorporated herein by reference.

The compounds described above or derivatives thereof are useful in treating disorders associated with activation of the TrkB receptor including neurological disorders, neuropsychiatric disorders, and metabolic disorders (e.g., obesity), as well as for promoting neuroprotection in humans, e.g., including pediatric and geriatric populations, and animals, e.g., veterinary applications. A subject in need of neuroprotection is a subject at risk for or having a neurologic or neuropsychiatric disorder. Neurologic or neuropsychiatric disorders include, for example, depression, anxiety, amyotrophic later sclerosis, Alzheimer's disease, Huntington's disease, Rett syndrome, epilepsy, Parkinson's disease, dementia, diabetic neuropathy, peripheral neuropathy, and central nervous system injuries. Central nervous system injuries include, for example, spinal cord injury, stroke, hypoxia, ischemia, and brain injury. As used herein the terms promoting, treating, and treatment includes prevention; delay in onset; diminution, eradication, or delay in exacerbation of one or more signs or symptoms after onset; and prevention of relapse.

The methods and compounds as described herein are useful for both prophylactic and therapeutic treatment. For prophylactic use, a therapeutically effective amount of the compounds described herein or derivatives thereof are administered to a subject prior to onset (e.g., before obvious signs of neurologic or neuropsychiatry disorder), during early onset (e.g., upon initial signs and symptoms of neurological disorder), or an established neurological disorder. Prophylactic administration can occur for several days to years prior to the manifestation of symptoms of a disorder, e.g., a neurological or a neuropsychiatry disorder. Prophylactic administration can be used, for example, in the preventative treatment of subjects diagnosed with genetic neurological disorders such as Huntington's disease or prior to surgery in which stroke and hypoxia is a risk. Therapeutic treatment involves administering to a subject a therapeutically effective amount of the compounds described herein or derivatives thereof after a disorder, e.g., a neurological disorder, neuropsychiatric disorder, or metabolic disorder (e.g., obesity), is diagnosed.

Administration of compounds described herein or derivatives thereof can be carried out using therapeutically effective amounts of the compounds described herein or derivatives thereof for periods of time effective to treat a disorder. The effective amount of the compounds described herein or derivatives thereof may be determined by one of ordinary skill in the art and includes exemplary dosage amounts for a mammal of from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

6. Combination Therapy

In these methods, the disorder being treated, e.g., depression, anxiety, central nervous system injury, metabolic disorder (e.g., obesity), or other disorder, can be further treated with one or more additional agents. The one or more additional agents and the compounds described herein or derivatives thereof can be administered in any order, including simultaneous administration, as well as temporally spaced order of up to several days apart. The methods may also include more than a single administration of the one or more additional agents and/or the compounds described herein or derivatives thereof. The administration of the one or more additional agents and the compounds described herein or derivatives thereof may be by the same or different routes and concurrently or sequentially. When treating with one or more additional agents, the 7,8-dihydroxyflavone with a modified flavone or heterocycle ring can be combined into a pharmaceutical composition with the one or more additional agents. For example, a 7,8-dihydroxyflavone with a modified flavone ring can be combined into a pharmaceutical composition with an anti-depressant, such as, for example imipramine, fluoxetine, paroxetine, and/or sertraline. As a further example, a 7,8-dihydroxyflavone with a modified flavone or heterocycle ring can be combined into a pharmaceutical composition with an anti-anxiolytic, such as, for example diazepam, alprazolam, clonazepam, and/or hydroxyzine.

The examples below are intended to further illustrate certain aspects of the methods and compounds described herein, and are not intended to limit the scope of the claims.

7. Kits

Typically, active ingredients of the pharmaceutical compositions of the disclosure are preferably not administered to a patient at the same time or by the same route of administration. This disclosure therefore encompasses kits which, when used by the medical practitioner, can simplify the administration of appropriate amounts of active ingredients to a patient.

A typical kit comprises a unit dosage form of a pharmaceutically acceptable salt of a TrkB agonist and optionally, a unit dosage form of a second pharmacologically active compound, such as anti-proliferative agent, or anti-cancer agent. In particular, the pharmaceutically acceptable salt of a TrkB agonist is the sodium, lithium, or potassium salt, or a polymorph, solvate, hydrate, dehydrate, co-crystal, anhydrous, or amorphous form thereof. A kit may further comprise a device that can be used to administer the active ingredient. Examples of such devices include, but are not limited to, syringes, drip bags, patches, and inhalers.

Kits of the disclosure can further comprise pharmaceutically acceptable vehicles that can be used to administer one or more active ingredients (e.g, a TrkB agonist). For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Other embodiments are directed to the use of the disclosed compositions in the preparation of a medicament for the treatment of a pathology ameliorated at least in part by BDNF signaling, particularly that which is mediated by TrkB.

8. Examples

Cells and Reagents

NGF and BDNF were from Roche. Anti-p-TrkB 817 was from Epitomics. Anti-TrkB antibody was from Biovision. Anti-TrkA was from Cell Signaling. TrkB$^{F616A}$ mice and wild-type C57BL/6 mice were bred in a pathogen-free environment in accordance with Emory Medical School guidelines. All chemicals not included above were purchased from Sigma. 7,8-dihydroxyflavone was purchased from TCI. The flavanoids were from Indofine (Hillsborough, N.J. 08833, USA). NMR spectrum (Bruker AV300K, 300 MHz), MS spectrum (Shimadzu LCMS), HPLC (PE, dual pumper, SPD detector, ODS—C18 reverse phase, 254 nm, CH3CN—H2O-0.1% TFA). Phospho-TrkB Y816 antibody was raised against [H]-CKLQNLAKASPV-pY-LDILG—[OH] (a.a. 806-822) (EM437 and EM438) as rabbit polyclonal antibody in Covance. Anti-phospho-TrkA 785, anti-TrkA, Phospho-Akt-473, anti-Akt and Anti-phospho-Erk1/2 antibodies were from Cell Signaling. Anti-p-TrkB Y817 antibody were from Epitomics.

Kainic Acid/TrkB Agonists Drug Administration

Male C57BL/6 mice aged of 60 days were orally injected with a single dose of 4'-DMA-7,8-DHF or 7,8-DHF (1 mg/kg each). KA (20 mg/kg) (Sigma, MO) was i.p. injected. Animals were continually monitored for 2 h for the onset of seizure activity. At 0, 4 and 8 h following TrkB agonist treatment, the animals were sacrificed and the hippocampal section lysates were analyzed by immunoblotting with p-TrkB, active caspase-3 and total TrkB antibodies.

Measuring Neuroprotective Effects of TrkB Agonists in TrkB F616A Mice

TrkB F616A knockin mice (2-3 months old) were fed with 1NMPP1 (25 mM) in drinking water one day before pharmacological reagent treatment. Next day, the mice were orally injected with 7,8-DHF or 4'-DMA-7,8-DHF (5 mg/kg) 4 h before kainic acid (20 mg/kg). The control mice were injected with saline, 1NMPP1, kainic acid alone or administrated 7,8-DHF or 4'-DMA-7,8-DHF 4 h before kainic acid. In 4 days, the mice were sacrificed and brains were homogenated and ultracentrafuged. The supernatant (40 mg) was employed for SDS-PAGE and immunoblotting analysis with indicated antibodies, respectively.

Immunohistochemistry Staining

Brain tissues were fixed in 4% paraformaldehyde overnight followed by paraffin embedding. Sections of 6 mm were cut. For immunohistochemical staining, brain sections were deparaffinized in xylene and rehydrated in graded alcohols. Endogenous peroxidase activity was blocked by 3% hydrogen peroxide for 5 minutes and all slides were boiled in 10 mM sodium citrate buffer (pH 6.0) for 10 minutes. Phosphorylated Trk B816 and Trk B were detected using specific antibodies. Paraffin section were deparaffinized in xylene and rehydrated gradient ethanol solution. Samples were boiled in 10 mM sodium citrate buffer for 20 min for antigen retrieval purpose. Brain sections were incubated with anti-TrkB (BD biosciences, San Jose, Calif.) 1:50, p-TrkB 1:300 dilution. Secondary antibodies were applied using anti-rabbit-Alexa 594 (red), anti-mouse-FITC (green). DAPI (blue) was used for nuclear staining Force Swim Test Adult male mice (2-3 months old) were randomly submitted to a forced swim test without a pre-swim. Saline, 4'-DMA-7,8-DHF and 7,8-DHF (5 mg/kg) were orally injected for 21 days. The mice were allowed to adapt to the test room for 2 days. The mice were placed in a clear glass cylinder with a diameter of 16 cm, half-filled with clear water at 24° C. (water depth of 14 cm did not allow the mice to reach the bottom of the cylinder; water was changed after each mouse) for a total of 6 min, and immobility was recorded during the last 4 min by an investigator blind to the genotype and treatment.

Analysis of Neurogenesis in TrkB Agonist-Treated Hippocampi

Adult male mice (2-3 months old) were orally injected with Saline, 4'-DMA-7,8-DHF and 7,8-DHF (5 mg/kg) for 21 days. Then Brdu (50 mg/kg) was i.p. injected. In 2 h, the mice were perfused with 4% paraformaldehyde. Immunohistochemical staining was performed on formalin-fixed paraffin-embedded sections. Sections from brain were cut, deparaffinized in xylene and rehydrated in graded alcohols. The slides were boiled in 10 mM citric acid (pH 6.0) for 10 min followed by an incubation in 2 N HCl for 10 min in room temperature. The slides were then permeabilized and blocked with 1% BSA in 0.2% PBST. The incorporated BrdU were stained using anti-BrdU-FITC (Abcam, USA) at 4° C. for 16 hr. After three washing in PBS, the cells were then stained with DAPI for another 10 min at room temperature. The slides were finally mounted with AquaMount (Lerner Laboratories, USA) containing 0.01% 1,4-diazobicyclo(2,2,2)octane and examined under a fluorescence microscope.

EXAMPLE 1

Organic Synthesis of 7,8-dihydroxyflavone Derivatives

Schemes 1-5 outline the synthetic strategies. Alternated compounds may be prepared by substitution of appropriate starting materials. 2-Hydroxy-3,4-dimethoxyacetophenone was first treated with pyridine and various benzoyl chloride under refluxing conditions, followed by an acid-induced dehydrative cyclization to generate the desired unprotected flavones. To synthesize the NH-replaced flavones in the middle C ring, a mixture of ethyl 3-(4-fluorophenyl)-3-oxopropanoate and 2,3-dimethoxybenzenamine were refluxed in the presence of AcOH (cat.) and $CaSO_4$ in EtOH (100 mL) at 75° C. under $N_2$, followed by cyclization and deprotection to generate the desired products.

The imidazole flavonoid was prepared according to scheme 5. To a mixture of N-(4-acetyl-3-hydroxy-2-nitrophenyl)acetamide (1, 1 g, 4.1 mmol, 1.0 eq) and triethylamine (1.5 mL) was added 4-(dimethylamino)benzoyl chloride (2 hydrochloride, 6.3 mmol, 1.5 eq.) in 3 portions at 0° C. Then the mixture was stirred at rt for 3 h. Diluted with DCM (100 mL), washed with 1N HCl (100 mL) and water (50 mL). The organic phase was separated, dried with sodium sulfate, filtered and concentrated to afford gray solid, which was purified by SGC (PE/EA=1/1) to afford (3-acetamido-6-acetyl-2-nitrophenyl 4-(dimethylamino)benzoate (3), 1.2 g, 75%).

A mixture of 3-acetamido-6-acetyl-2-nitrophenyl 4-(dimethylamino)benzoate (3, 2 g, 1.0 eq.) and potassium hydroxide (8 g, 2.0 eq.) in pyridine (20 mL) was heated to 60° C. for 1 h and poured into icy 1N HCl (100 mL). The yellow solid was collected and dissolved in acetic acid (20 mL) and concentrated sulfuric acid. The resulting mixture was heated to 110° C. for 30 min. The mixture was cooled to rt and poured into sat.sodium carbonate. The yellow solid was filtered and dried in vacuo to afforded 7-amino-2-(4-(dimethylamino)phenyl)-8-nitro-4H-chromen-4-one (4) (1.5 g, yield:89%)

A solution of 7-amino-2-(4-(dimethylamino)phenyl)-8-nitro-4H-chromen-4-one (4, 900 mg, 2.77 mmol) and 10% Pd/C (450 mg) in methanol (9 mL) and concentrated hydrochloride (aq., 9 mL) was stirred at the atmosphere of hydrogen overnight. The solid was filtered and the filtrate was evaporated in reduced pressure to afford 7,8-diamino-2-(4-(dimethylamino)phenyl)-4H-chromen-4-one hydrochloride (5) as a light yellow solid (810 mg, yield: 88%).

A solution of 7,8-diamino-2-(4-(dimethylamino)phenyl)-4H-chromen-4-one hydrochloride (500 mg) in HCO2H (5 mL) was heated to reflux for 1 h. The volatiles were evaporated in reduced pressure and the residue partitioned between EA/i-PrOH=20/1 (50 mL) and sat. sodium carbonate (25 mL). The organic phase was separated, dried with sodium sulfate, filtered and concentrated to afford yellow solid, which was recrystallized from EA (25 mL) to afford light yellow solid (111 mg, yield: 24%). 8-(4-(dimethylamino)phenyl)chromeno[7,8-d]imidazol-6(1H)-one (6). $^1$H NMR (300 MHz, DMSO-$d_6$) δ 8.46(m, 1H), 10.09(br s, 1H), 8.01(m, 2H), 7.82 (m, 1H), 7.61 (m, 2H), 6.84~6.88(m, 3H), MS-ESI: cal. 305; found: 306(M+H)–. HPLC: 99.23%

EXAMPLE 2

Structure-Activity Relationship Study of 7,8-dihydroxyflavone (7,8-DHF)

Figure 1B:
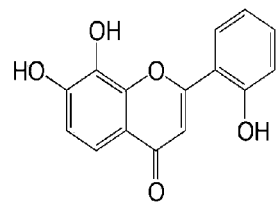
FIG. 1B illustrates the chemical structures of flavonoids.
Figure 1B:
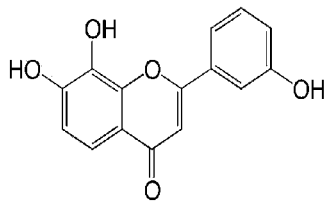
Figure 1B:
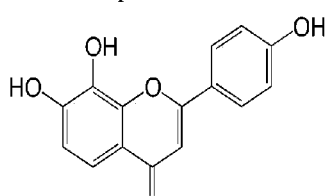
Figure 1B:
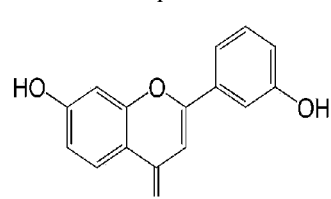
Figure 1B:
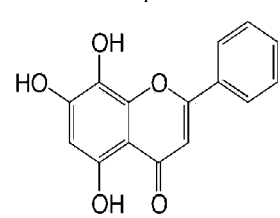
Figure 1B:
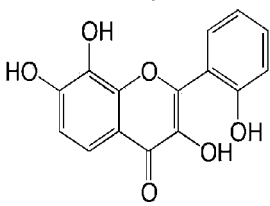
Figure 1B:
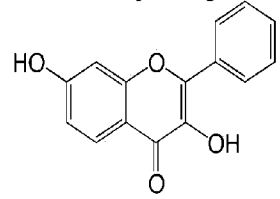
Figure 1B:
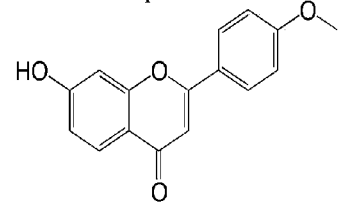
Figure 1B:
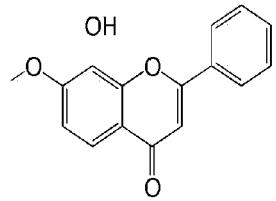
Figure 1B:
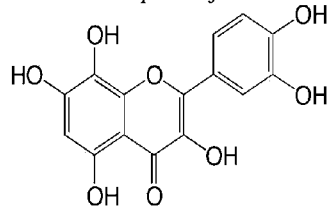
Figure 1C:
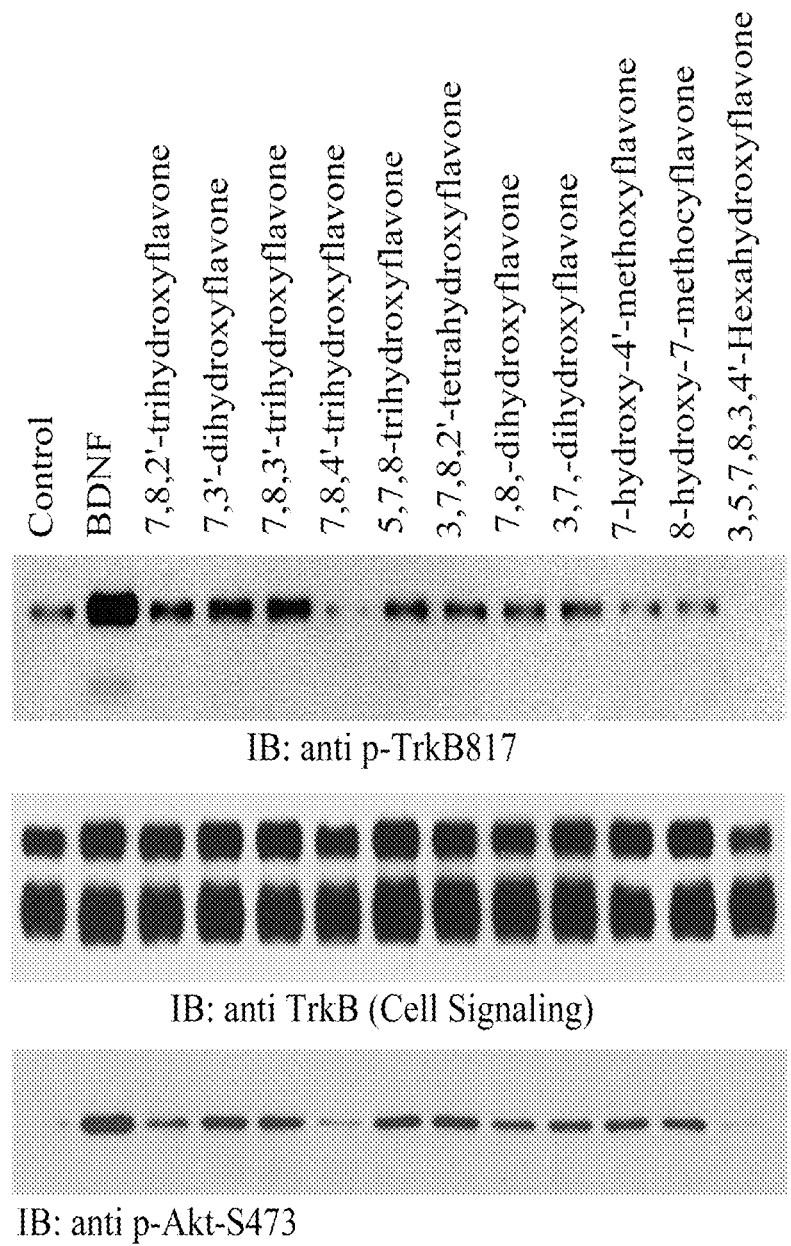
FIG. 1C shows data of immunoblotting analysis with neuronal lysates. Primary rat cortical neurons from E17 embryos (13 DIV) were treated with 500 nM various chemicals for 15 min. The neuronal cell lysates were collected and resolved on 10% SDS-PAGE. Immunoblotting was conducted with various antibodies. p-TrkB Y817 antibody was employed at 1:20000-40000 dilution.
Figure 1D:
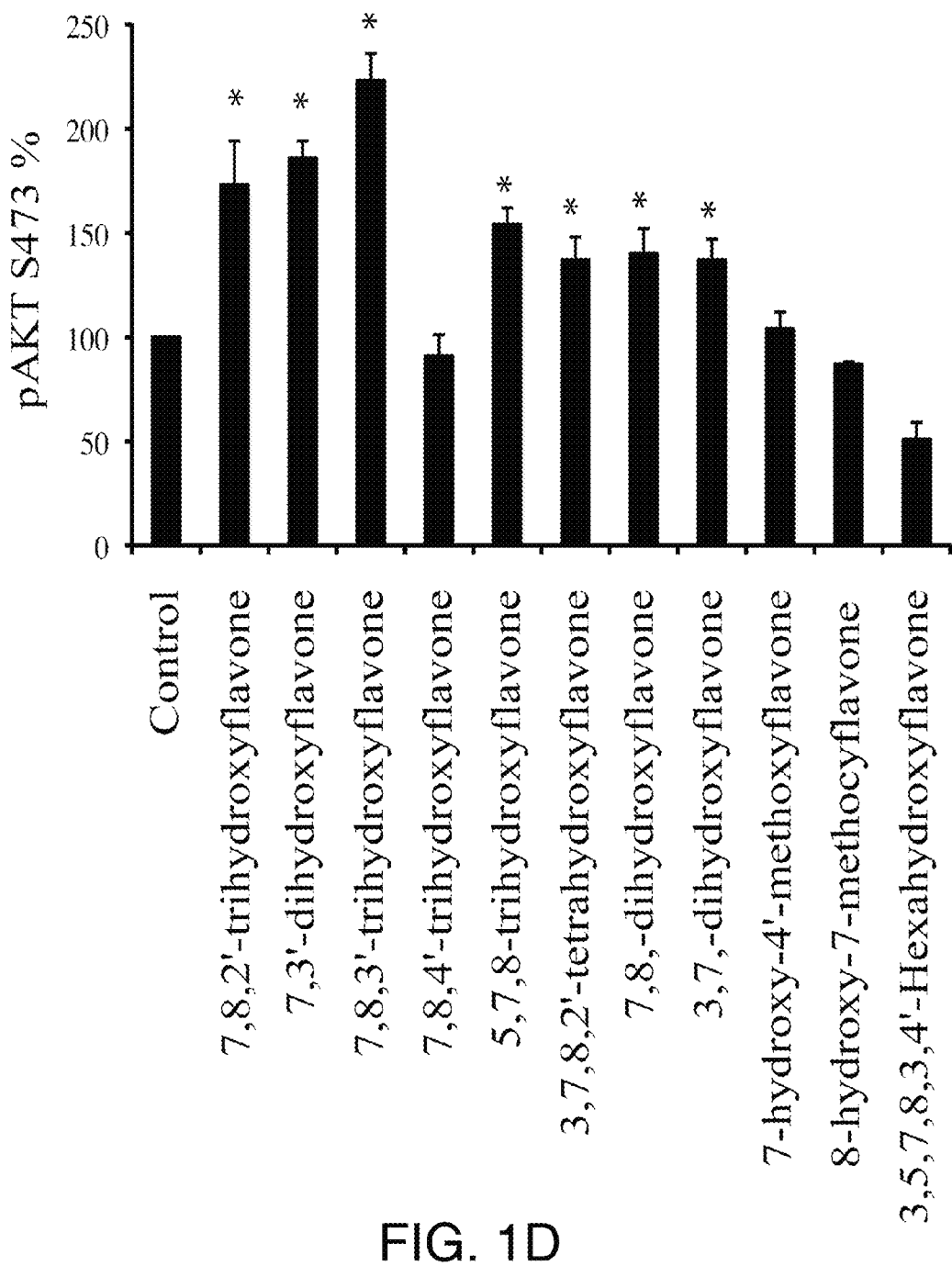
FIG. 1D shows data on Phospho-Akt 473 ELISA. The cell lysates (20 µg/sample) from the neurons treated with various indicated drugs were analyzed by p-Akt ELISA. The quantitative p-Akt activity in ELISA correlated with TrkB activity. Results were expressed as mean (SEM(*$P<0.05$, compared with the vehicle control group, Student t test, n=3).

7,8-dihydroxyflavone (7,8-DHF) is a small molecular TrkB agonist. Preliminary structure-activity relationship study (SAR) supports that 7,8-catechol moiety is essential for the agonistic effect by 7,8-DHF. To explore the structure-activity relationship (SAR) in depth, the TrkB stimulatory activity was examined by numerous flavonoid derivatives. The numeric positions and each ring's nomenclature are designated (FIG. 1A). Compounds were dissolved in DMSO, then diluted into 500 mM with 1× PBS (final vehicle contains 10% DMSO/PBS) (FIG. 1B). Primary rat cortical neurons were treated with 500 nM compounds for 20 min. The cell lysates were analyzed by immunoblotting. Neurons treated with BDNF (100 ng/ml) strongly activated TrkB, as TrkB was robustly phopshorylated. 7,8,2'-trihydroxyflavone, 5,7,8-trihydroxyflavone, 3,7,8,2'-tetrahydroxyflavone, 7,8-dihydroxyflavone (7,8-DHF) and 3,7-dihydroxyflavone all stimulated TrkB activation when compared to controls (FIG. 1C, top panel lane 3 and 7-10). 7,3'-dihydroxyflavone and 7,8,3'-trihydroxyflavone displayed even more robust stimulatory effect on TrkB phosphorylation than the lead, previously identified 7,8-DHF (FIG. 1C, top panel lane 4-5). By contrast, 7,8,4'-trihydroxyflavone, 7-hydroxy-4'methoxyflavone and 8-hydroxy-7-methoxyflavone barely activated TrkB as compared to vehicle control (FIG. 1C, top panel lane 6, 11 and 12). The highly hydroxylated flavone derivative, 3,5,7,8,3',4'-hexahydroxylatedflavone completely blocked TrkB phosphorylation (FIG. 1C, top panel, last lane). Downstream activation of the TrkB target Akt was tightly correlated with TrkB activation patterns by these derivatives (FIG. 1C, bottom panel). As observed, the hydroxy groups on B ring can regulate 7,8-DHF's stimulatory activity on TrkB receptor. As 2'-hydroxy, especially 3'-hydroxy group, elevates the agonistic effect, whereas 4'-hydroxy group diminishes its stimulatory effect.

EXAMPLE 3

Figure 2A:
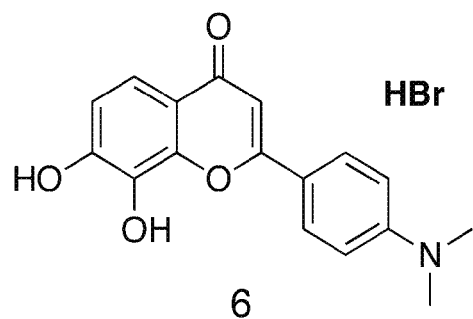
FIG. 2A illustrates the chemical structures of various 7,8-DHF derivatives.
Figure 2A:
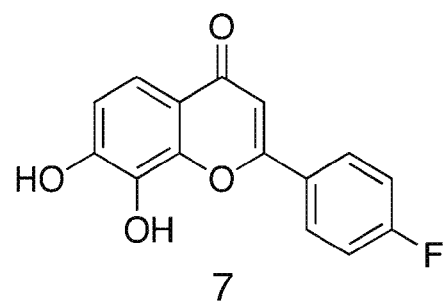
Figure 2A:
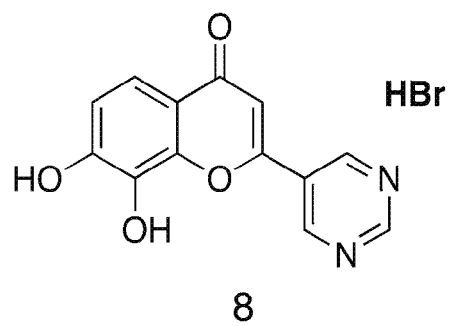
Figure 2A:
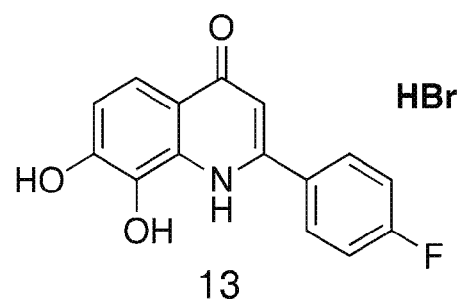
Figure 2A:
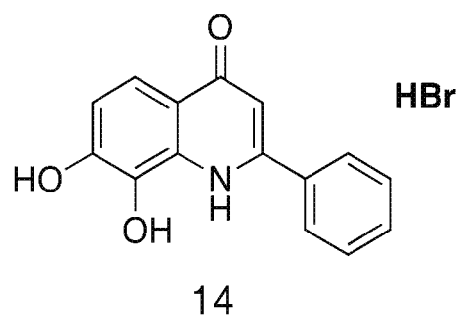
Figure 2B:
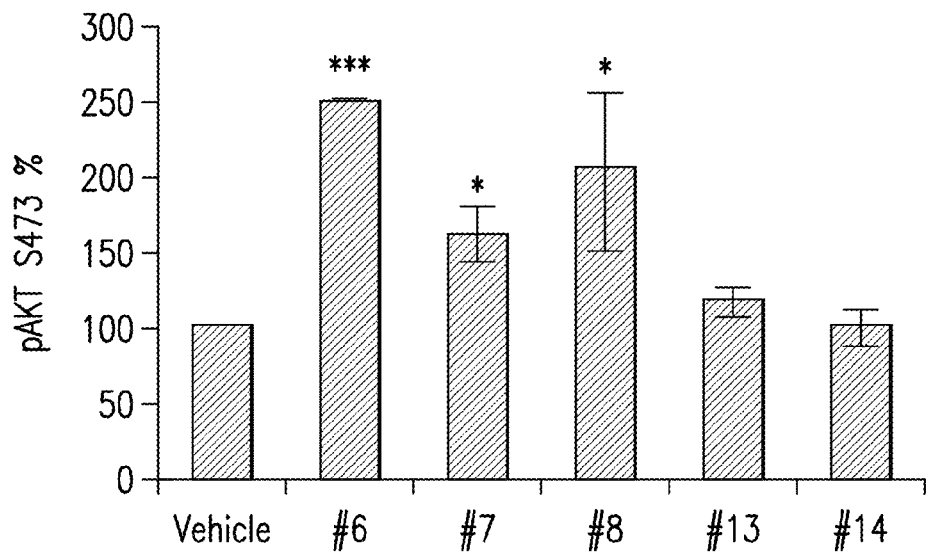
FIG. 2B shows data indication TrkB stimulatory effects of 7,8-dihydroxyflavone and 7,8-dihydroxyflavone derivatives. 4'-Dimethylamino-7,8-dihydroxyflavone displays more potent TrkB stimulatory effect than parental 7,8-dihydroxyflavone. Phospho-Akt ELISA assay by the synthetic compounds in cortical neurons. Primary cortical cultures from E11 rat embryos were treated with 500 nMof various 7,8-DHF derivatives. The cell lysates were analyzed by the ELISA (left panel) (*, $P<0.05$; ***, $P<0.001$ vs vehicle, Student's t test). Different doses of 4'-DMA-7,8-DHF and 7,8-DHF were incubated with primary cortical neurons for 15 min. The cell lysates (20 µg) were analyzed with p-Akt ELISA (right panel) (*, $P<0.05$; , $P<0.01$; *, $P<0.001$ vs control; one-way ANOVA: b, $P<0.01$; c, $P<0.001$ vs 7,8-DHF at same concentration, Student's t test). The data were from two sets of replicated experiments.
Figure 2B:
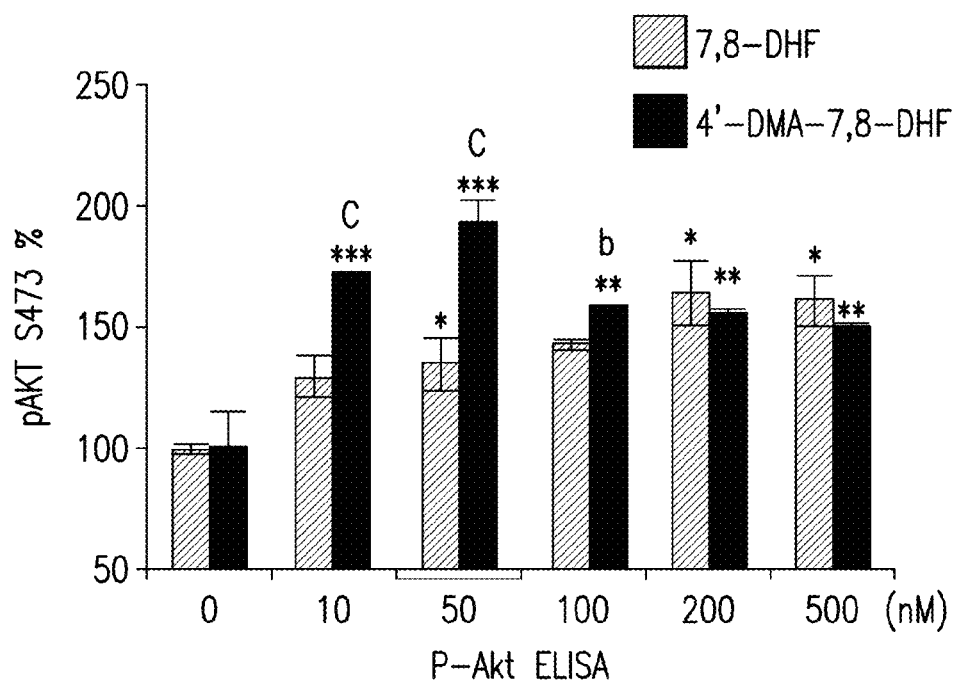
Figures 1, 2C:
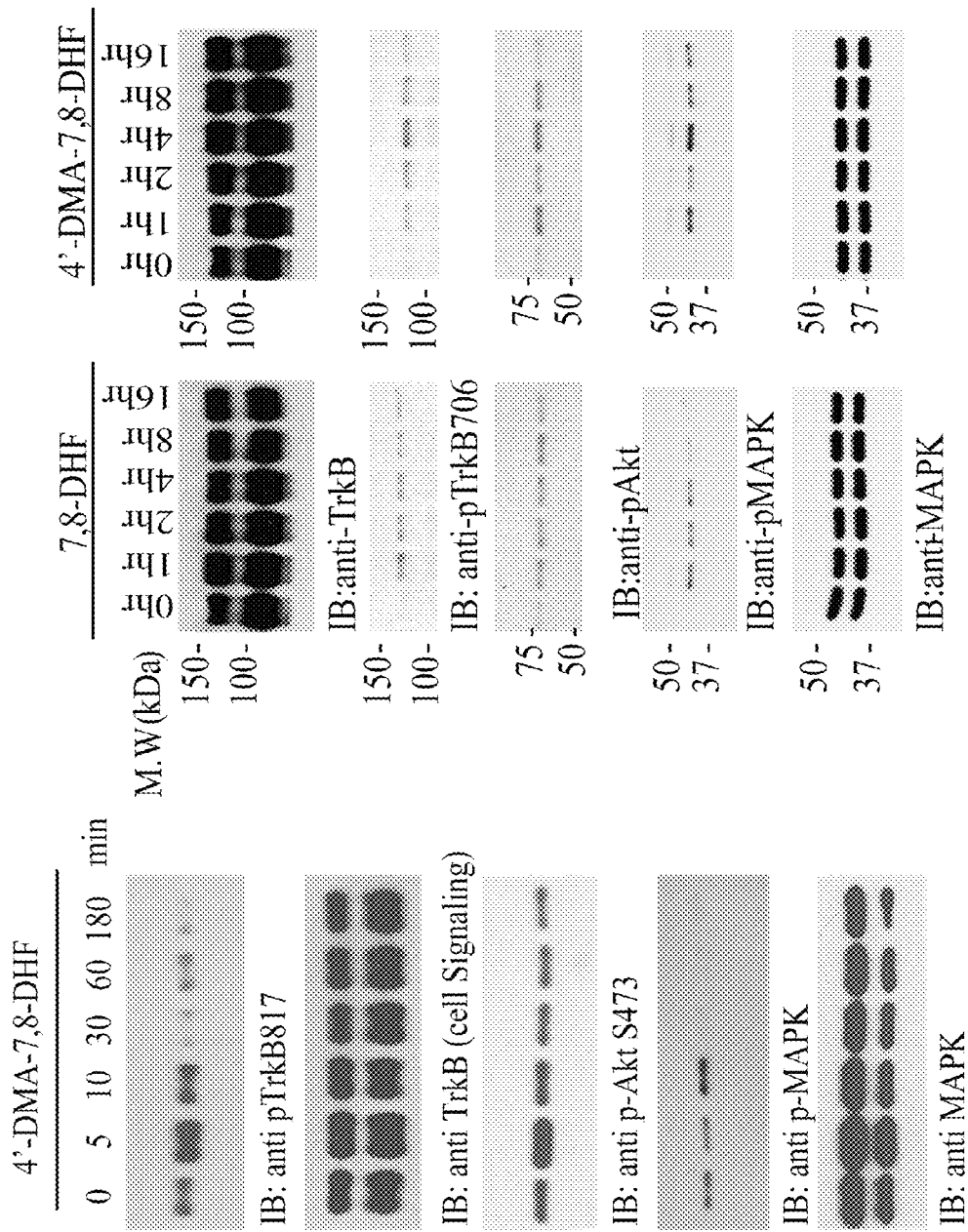
FIG. 2C-1 shows data from time course assay with 4'-DMA-7,8-DHF. Rat primary neurons were treated with 500 nM. 4'-DMA-7,8-DHF from various time points. The neuronal lysates were analyzed with various antibodies. 4'-DMA-7,8-DHF rapidly activated TrkB and its downstream signaling cascades (left panels). 4'-DMA-7,8-DHF revealed longer period of TrkB activation in mouse brain. One mg/kg of 4'-DMA-7,8-DHF and 7,8-DHF were orally administrated into C57 BL/6J mice and TrkB phosphorylation and its downstream signaling cascades including Akt and MAPK in mouse brain were analyzed by immunoblotting at various time points. TrkB activation by 4'-DMA-7,8-DHF peaked at 4 h, whereas the maximal TrkB activation by 7,8-DHF in mouse brain occurred at 1-2 h (middle panels).
Figures 2, 2C:
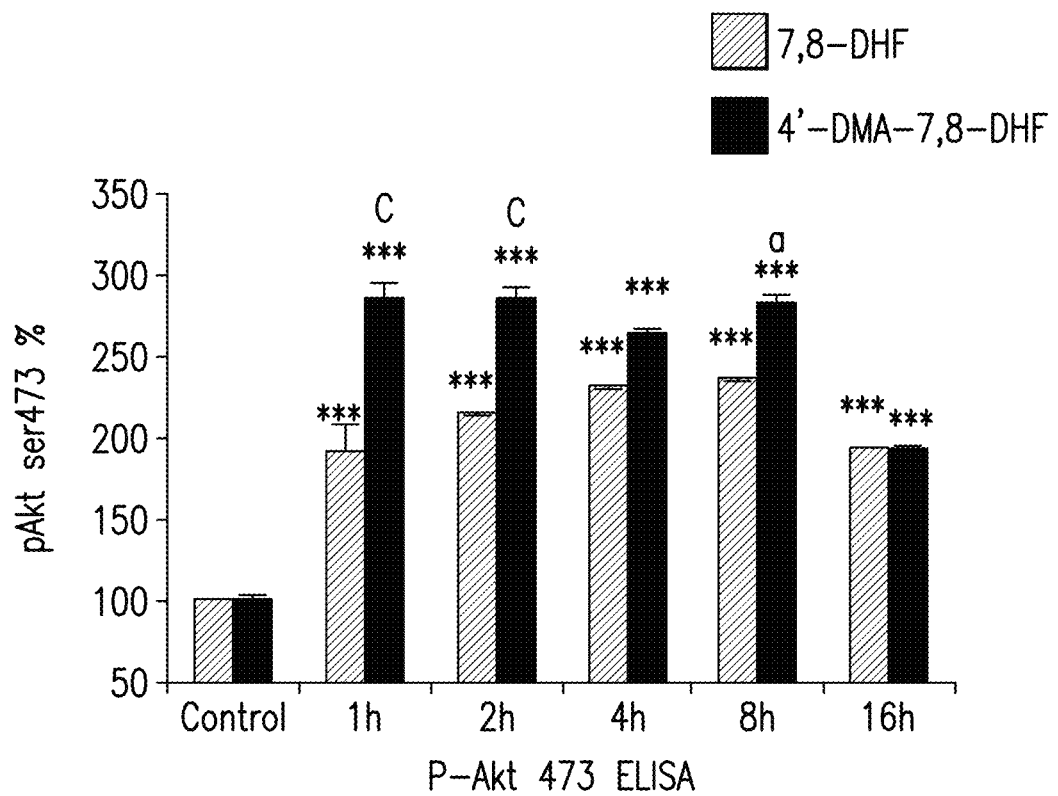
Figure 2D:
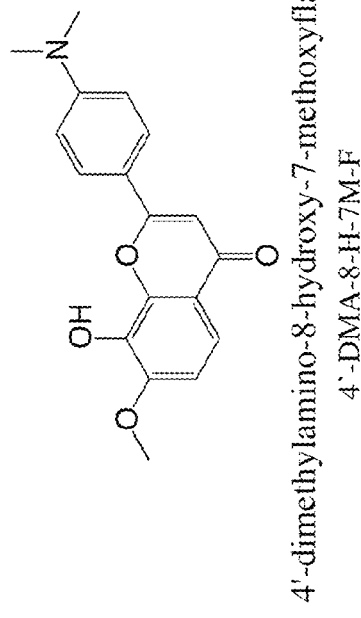
FIG. 2D shows data indicating 7,8-Dihydroxy groups are important for the flavone's agonistic effect. Different methoxy replaced derivatives were tested on primary neurons by immunoblotting assays.
Figure 2D:
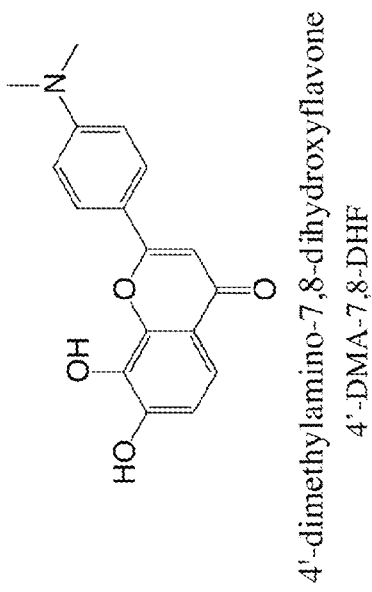
Figure 2D:
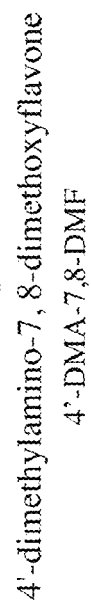
Figure 2D:
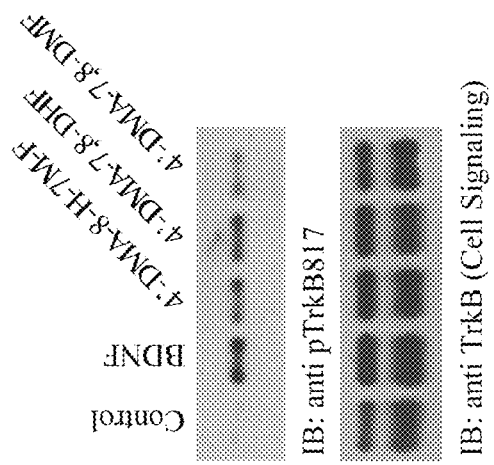

7,8-Dihydroxyflavone Derivatives Display More Potent TrkB Stimulatory Effect than Parental 7,8-dihydroxyflavone To compare the TrkB activation by these synthetic compounds, primary cortical cultures were prepared. Cortical neurons were treated with 500 nM of various compounds for 20 min and cell lysates were collected. Immunoblotting analysis revealed that 4'-dimethylamino-7,8-dihydroxyflavone (#1, 4'-DMA-7,8-DHF) and 7,8-dihydroxy-2(pyrimidin-5-yl)-4H-chromen-4-one (#4) strongly activated TrkB, whereas 2-(4-fluorophenyl)-7,8-dihydroxyquinolin-4(1H)-one (#2) and 7,8-dihydroxy-2-phenylquinolin-4(1H)-one (#3) failed to provoke TrkB activation (FIGS. 2A & B). These data suggest that the 0 atom in the middle C ring is important for 7,8-DHF's agonistic effect. Replacing the H-bond acceptor O atom with hydrogen bond donor NH abolishes its stimulatory effect. Titration assays demonstrated that 4'-DMA-7,8-DHF triggered TrkB activation at a concentration as low as 10 nM, and TrkB activity gradually increased as drug concentration escalated. On the other hand, 7,8-DHF provoked TrkB activation with the minimal concentration of 100 nM (FIG. 2B, right panels). To further study 4'-DMA-7,8-DHF's kinetics on TrkB activation, primary neurons were treated for various time points. 4'-DMA-7,8-DHF swiftly activated TrkB as soon as 5 minutes following treatment. Activated signal slightly reduced at 10 min, and decayed back to baseline at 30-180 min (FIG. 2C, top panel). Akt activation pattern temporally coupled to TrkB activation (FIG. 2C, $3^{rd}$ panel). MAPK phosphorylation was observed to peak at 10 min following treatment (FIG. 2C, $4^{th}$ panel). To compare the stimulatory effect on TrkB receptor in mouse brains, 1 mg/kg of the synthesized derivatives were injected into C57BL/6J mice. TrkB activation was monitored at different time points. 4'-DMA-7,8-DHF elicited TrkB activation at 1 h and the activity of TrkB gradually escalated with the time and peaked at 8 h and partially decayed at 16 h. By contrast, the parental 7,8-DHF triggered TrkB activation slightly later, approximately 2 h after oral injection, where it peaked at 4 h and progressively decreased. Elevated TrkB activity was demonstrable even at 16 h (FIG. 2C, right panels). Thus, 4'-DMA-7,8-DHF possesses about 10-fold higher agonistic effect on TrkB than the parental compound 7,8-DHF and its agonistic effect is sustained longer in animals as well.

EXAMPLE 4

Figure 3A:
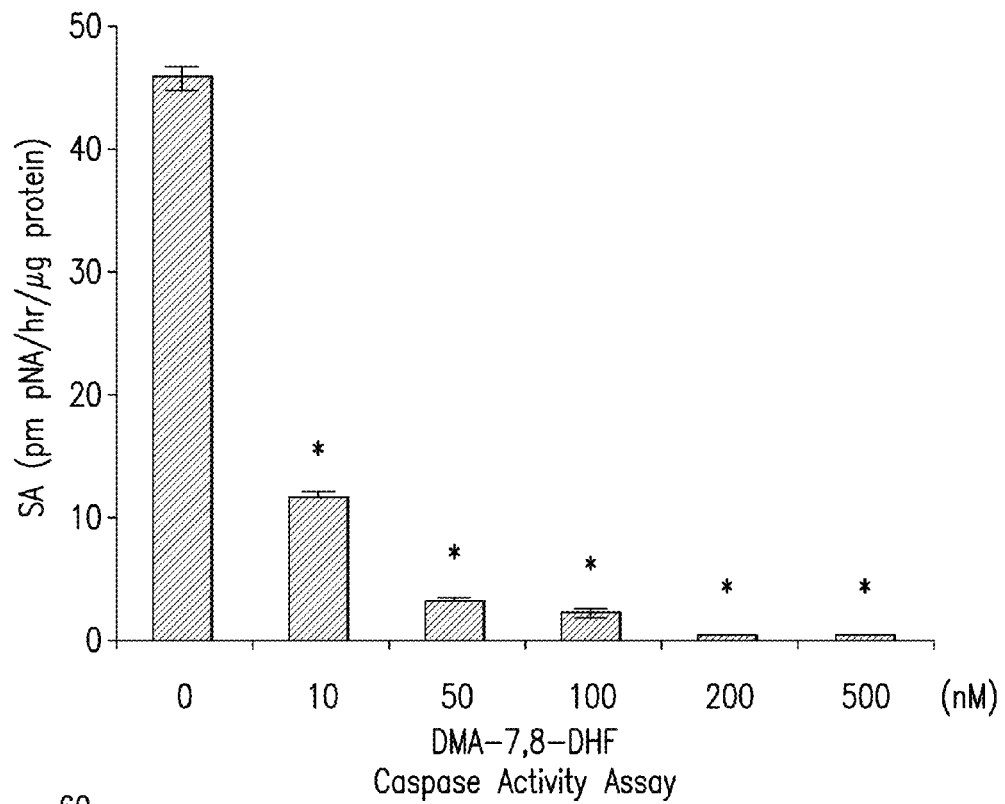
FIG. 3A shows data from active caspase-3 ELISA assay indicating the neuroprotective effects of 7,8-dihydroxyflavone derivatives. 4'-Dimethylamino-7,8-dihydroxyflavone prevents neurons from apoptosis in a TrkB-dependent manner. Cortical neurons were prepared from E16 rat embryonic. The neurons were pretreated with different doses of compounds as indicated for 30 min, followed by 50 µM glutamate for 16 h. The cell lysates were analyzed by active caspase-3 ELISA.
Figure 3B:
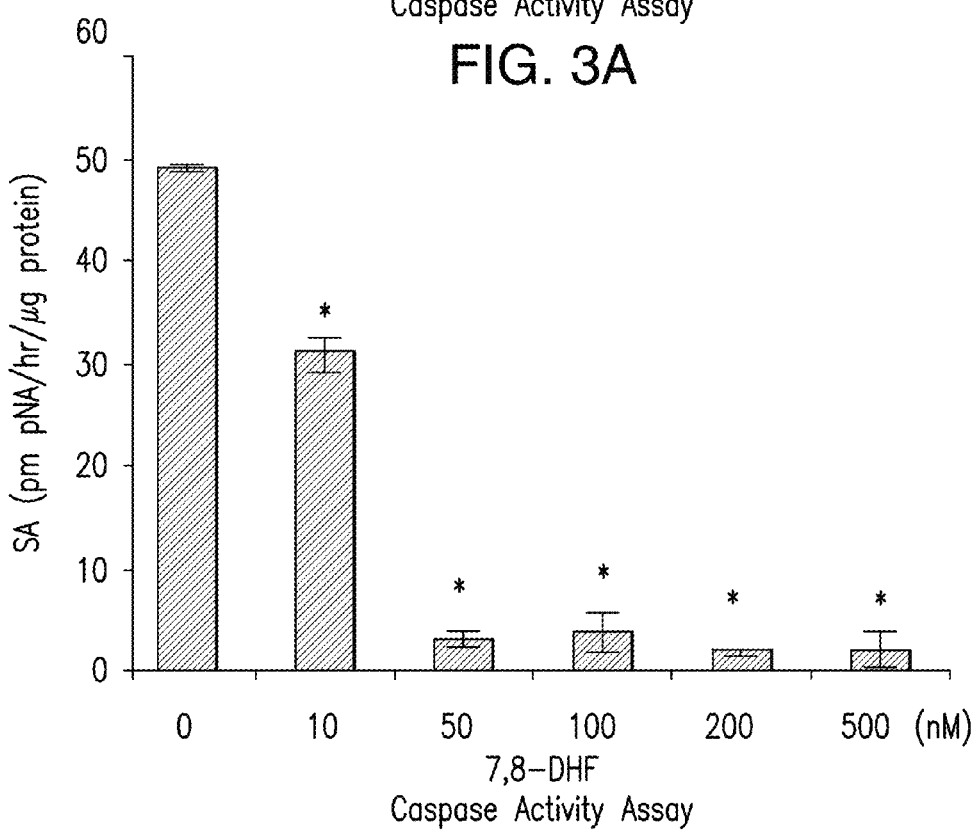
FIG. 3B shows data from active caspase-3 ELISA assay for 7,8-dihydroxyflavone as in FIG. 3A.
Figure 3D:
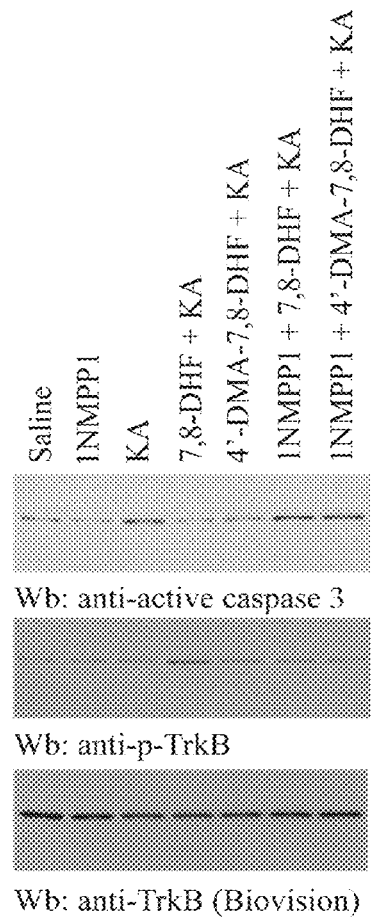
FIG. 3D shows data indicating TrkB activation is indispensable for the neuroprotective effect of 4'-DMA-7,8-DHF. 4'-DMA-7,8-DHF and 7,8-DHF suppressed KA-induced caspase-3 activation in TrkB F616A mutant knockin mice, which cannot be blocked by 1NMPP1 (top panel). TrkB F616A was strongly activated by 4'-DMA-7,8-DHF and 7,8-DHF, which was blocked by 1NMPP1 (middle panel).
Figure 3C:
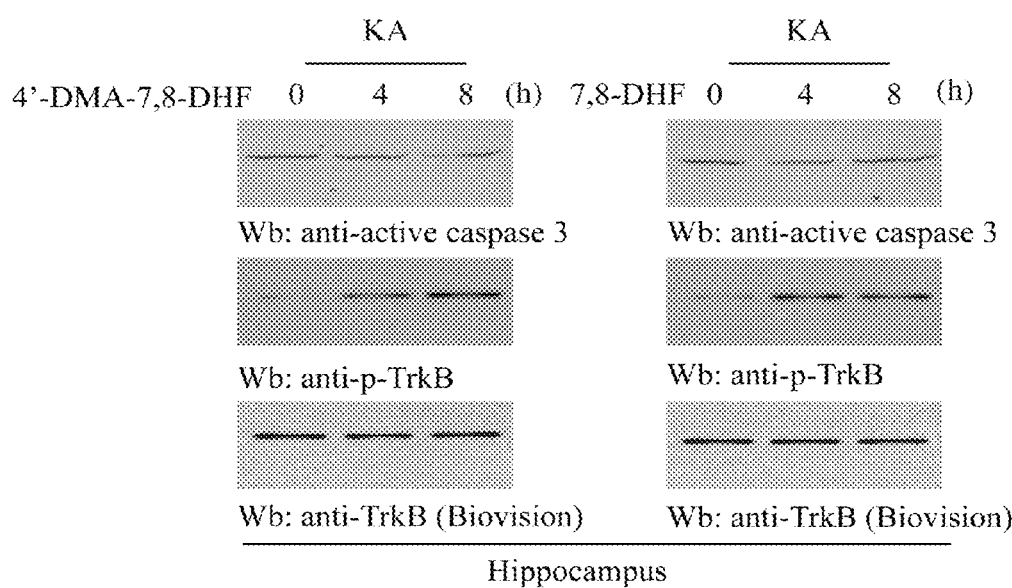
FIG. 3C shows data indicating 4'-DMA-7,8-DHF and 7,8-DHF prevent KA-elicited neuronal cell death. C57BL/6J mice were orally administrated with 5 mg/kg of 4'-DMA-7,8-DHF and 7,8-DHF; at different time points, the mice were ip injected with 20 mg/kg KA for 2 h. The brain lysates were analyzed by immunoblotting with anti-p-TrkB, anti-active caspase-3 antibodies, respectively.
Figure 4A:
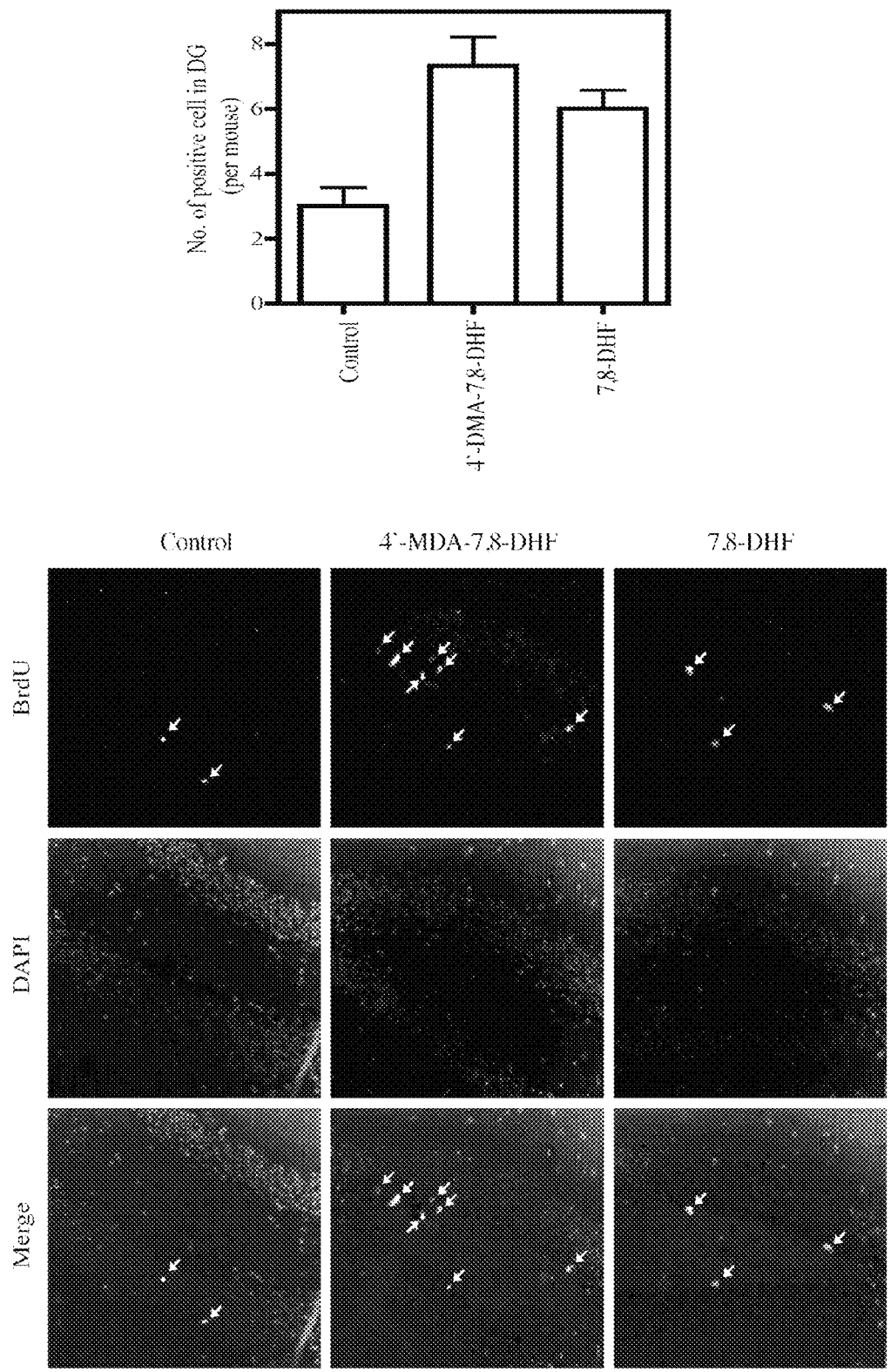
FIG. 4A shows data from neurogenesis assay indicating neurogenic effects of 7,8-dihydroxyflavone and 7,8-dihydroxyflavone derivatives. 4'-Dimethylamino-7,8-dihydroxyflavone and 7,8-dihydroxyflavone promote neurogenesis. Male C57BL/6J mice were orally administrated with 5 mg/kg 4'-DMA-7,8-DHF and 7,8-DHF and vehicle solvent for 21 days and followed by 50 mg/kg BrdU ip injection. In 2 h, the mice were perfused and brain sections were immunostained with anti-BrdU and DAPI. The positive cells in dentate gyms were highlighted by arrow (left panels). Quantitative analysis of the BrdU positive cells in dentate gyms (right panel).

4'-dimethylamino-7,8-dihydroxyflavone Possesses More Robust Anti-Apoptotic Activity than the Lead Compound To quantitatively compare the anti-apoptotic activity by these two TrkB agonists, cortical neurons were pretreated with various concentrations of 4'-DMA-7,8-DHF and 7,8-DHF for 30 min, followed by 50 mM glutamate for 16 h. Cell lysates were quantitatively analyzed with an active caspse-3 ELISA. Both compounds at 50 nM or higher concentrations substantially blocked caspase-3 activation. However, at 10 nM, 4'-DMA-7,8-DHF displayed a more robust inhibitory effect than 7,8-DHF (FIGS. 4A & B). To investigate whether these compounds exert any neuroprotective effects in animals, both compounds (5 mg/kg) were orally injected into mice. At 0, 2 h or 6 h, kainic acid (KA)(20 mg/kg) was administered intraperitoneally. At 2 h, mice were sacrificed and hippocampal regions were prepared. Immunoblotting with mouse brain lysates demonstrated that KA-induced neuronal apoptosis was gradually decreased over time, which inversely correlated with TrkB activation by 4'-DMA-7,8-DHF (FIG. 3C, left panels). KA-induced caspase-3 activation was reduced at 4 h by 7,8-DHF, and active caspase-3 was slightly increased at 8 h. This kinetic spectrum tightly coupled to the TrkB activation status observed when treated with 7,8-DHF (FIG. 3C, right panel).

TrkB F616A knock-in mice were then used to demonstrate that the neuroprotective action of 7,8-DHF derivatives is dependent on TrkB activation in vivo. TrkB F616A can be selectively blocked by 1NMPP1, a TrkB F616A inhibitor, resulting in a TrkB-null phenotype (Schmidt et al., 2007). Since 1NMPP1 selectively inhibits TrkB F616A activation by 7,8-DHF, blockage of TrkB F616A signaling by 1NMPP1 in mice was reasoned to make neurons vulnerable to KA-provoked neuronal cell death. KA treatment alone caused significant caspase-3 activation, which was markedly diminished by 4'-DMA-7,8-DHF and 7,8-DHF pretreatment. Interestingly, 1NMPP1 pretreatment abolished 4'-DMA-7, 8-DHF and 7,8-DHF's protective effect in F616A mice (FIG. 3D, top panel). Accordingly, TrkB phosphorylation by 4'-DMA-7,8-DHF and 7,8-DHF was notably blocked by 1NMPP1 pretreatment (FIG. 3D, $2^{nd}$ panel). These data demonstrate that 4'-DMA-7,8-DHF and 7,8-DHF selectively activate TrkB receptor and enhance neuronal survival in mice.

EXAMPLE 5

Figure 4B:
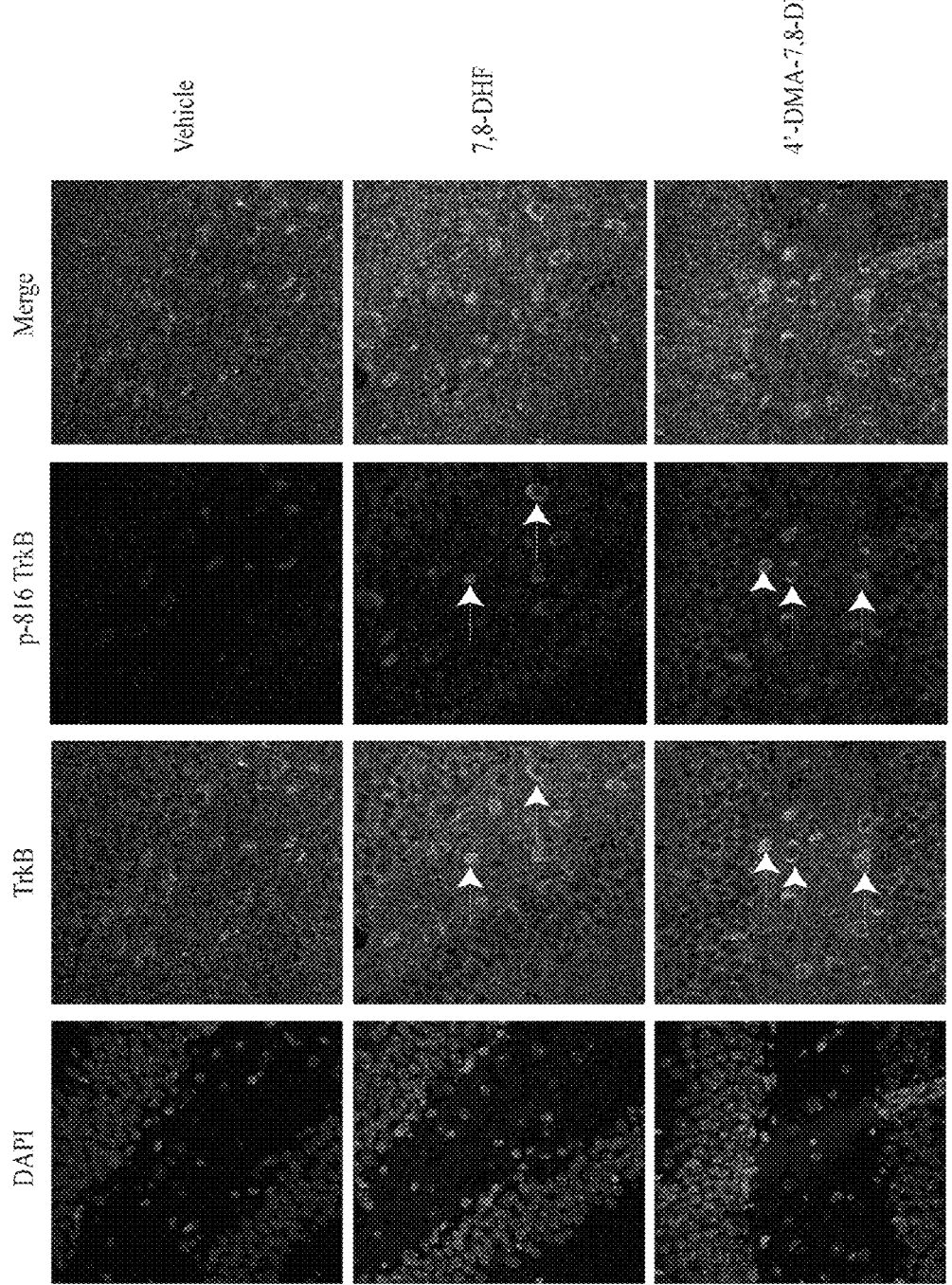
FIG. 4B shows data indicating 7,8-DHF and its derivative upregulate TrkB activation in dentate gyrus. Paraffin section were deparaffinized in xylene and rehydrated gradient ethanol solution. Samples were boiled in 10 mM sodium citrate buffer for 20 min for antigen retrieval purpose. Brain sections were incubated with anti-TrkB (BD biosciences, San Jose, Calif.) 1:50, and anti-p-TrkB Y816 was used at 1:300 dilution. Secondary antibody were applied using antirabbit-Alexa 594 (red), antimouse-FITC (green). DAPI (blue) was used for nuclear staining.

4'-dimethylamino-7,8-dihydroxyflavone and 7,8-dihydroxyflavone Promote Neurogenesis Administration of chronic, but not acute, monoamine antidepressant drugs enhances adult neurogenesis in dentate gyrus of rodents and non-human primates, while blocking neurogenesis by irradiation attenuates the behavioral antidepressant-like effects of these drugs in some rodent strains. This has led to models suggesting that enhancement of adult hippocampal neurogenesis is important for the efficacy of antidepressant drugs. Ablation of TrkB specifically in hippocampal neural progenitor cells prevents chronic antidepressant-induced neurogenesis and renders the mice behaviorally non-responsive to chronic antidepressant treatment. To test whether increasing TrkB activation by these small agonists would elevate the neurogenesis, adult male C57BL/6J mice were orally injected with either vehicle, 7,8-DHF, or 4'-DMA-7,8-DHF (5 mg/kg) for 21 days. At the end of treatment (day 21), animals were injected with BrdU (50 mg/kg, intraperitoneally) to label dividing cells and were sacrificed 2 h later. BrdU immunohistochemistry was used to assess progenitor proliferation (FIG. 4A). Treatment with TrkB agonists significantly increased neurogenesis as compared to vehicle control. Immunohistochemistry demonstrated that TrkB was markedly activated by both 7,8-DHF and 4'-DMA-7,8-DHF in the dentate gyrus (FIG. 4B) after 21 days treatment. Therefore, chronic treatment with TrkB agonists promotes neurogenesis in the hippocampus of mice.

EXAMPLE 6

Figure 5A:
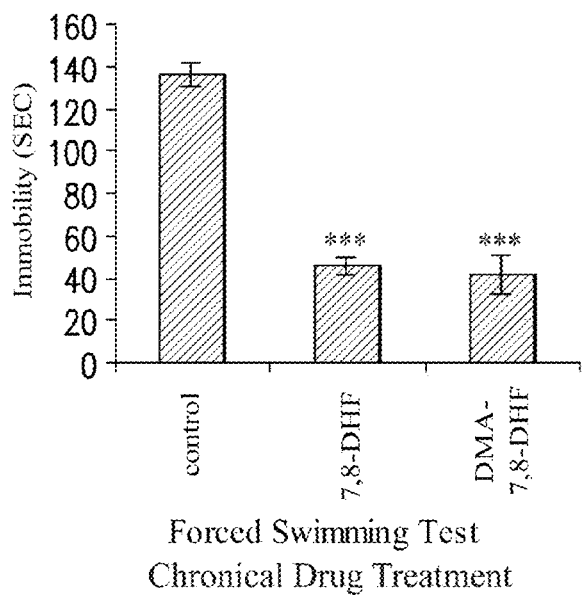
FIG. 5A shows data from forced swim test with 4'-DMA-7,8-DHF and 7,8-DHF compounds indicating antidepressive effects of 7,8-dihydroxyflavone and 7,8-dihydroxyflavone derivatives. 4'-Dimethylamino-7,8-dihydroxyflavone and 7,8-dihydroxyflavone demonstrate antidepressant effect in a TrkB-dependent manner. Male C57BL/6J mice (8 mice/group) were orally administrated by gavage with 5 mg/kg 4'-DMA-7,8-DHF and 7,8-DHF and vehicle solvent saline for 21 days and subjected to a forced swim test (6 min, immobility recorded in the last 4 min). Data are presented as mean±SEM. Analysis of variance (ANOVA) revealed significant difference between vehicle and either 7,8-DHF or 4'-DMA-7,8-DHF (n=6, ***P<0.0001 vs vehicle).
Figure 5C:
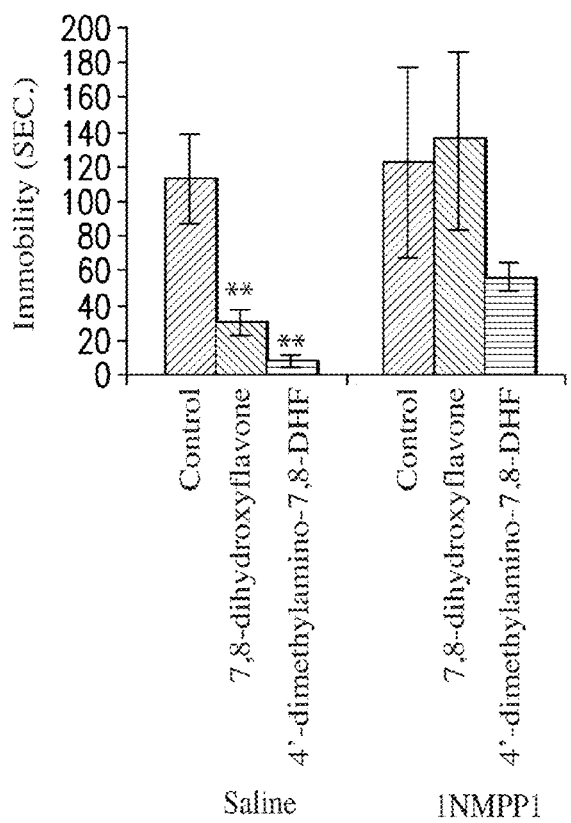
FIG. 5C shows data from forced swim test with TrkB F616A knockin mice. Male TrkB knockin mice were given the regular drinking water or 1NMPP1 (25 µM) containing drinking water one day before we started to inject the drugs and sustained throughout the whole experiment. The indicated control (saline) and drugs were administrated for 5 days. Data are presented as mean±SEM; analysis of variance (ANOVA) revealed significant effect between vehicle and either 7,8-DHF (n=7 mice, P<0.001) or 4'-DMA-7,8-DHF (P<0.001) in TrkB KI mice. None of the drugs produced a significant change in 1NMPP1 treated TrkB KI mice (n=6 to 7 mice) as compared to control.
Figure 5B:
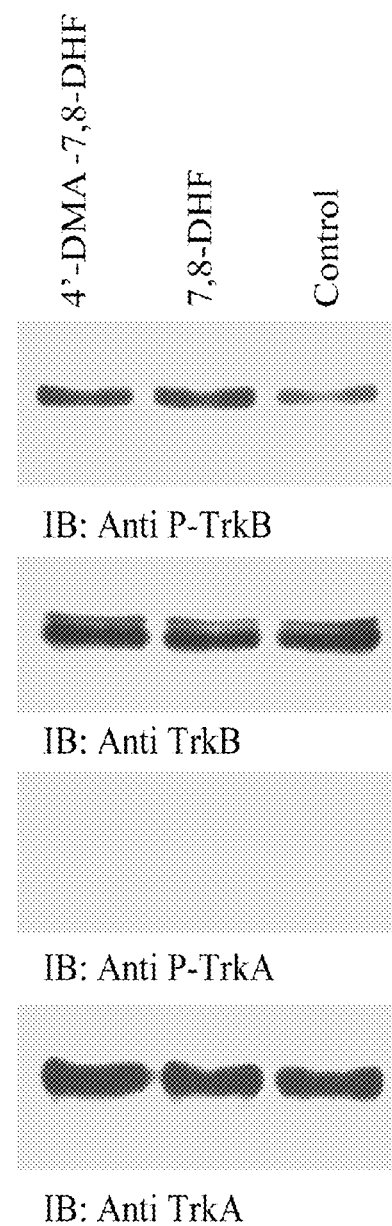
FIG. 5B shows data indicating TrkB but not TrkA is activated by 4'-DMA-7,8-DHF and 7,8-DHF in mouse brain. The brain lysates from above chronically treated mice were analyzed by immunoblotting with anti-p-TrkA 794 and p-TrkB 817.

4'-dimethylamino-7,8-dihydroxyflavone Demonstrates Antidepressant Effects in a TrkB-Dependent Manner Accumulating evidence supports that BDNF plays a role in mediating therapeutic effects of antidepressants. Infusion of exogenous BDNF into hippocampus or brain stem has anti-depressant-like behavioral effect. A forced swim test is broadly used for screening of potential antidepressant drugs and is widely used to measure antidepressant activity. To explore whether 4'-DMA-7,8-DHF and 7,8-DHF have any antidepressant effect like BDNF, a forced swim test was conducted after chronic treatment of the mice for 21 days via oral injection. When mice were treated with 7,8-DHF (5 mg/kg), the swimming immobility was significantly decreased. Interestingly, 4'-DMA-7,8-DHF (5 mg/kg) also evidently reduced the immobility (FIG. 6A), suggesting that both 7,8-DHF and 4'-DMA-7,8-DHF imitate BDNF and exert potent anti-depressant effect. Immunoblotting analysis revealed that both compounds evidently provoked TrkB but not TrkA activation in mouse brain (FIG. 5B).

TrkB F616A knockin mice were used to assess whether the behavior responses by 7,8-DHF and its derivative is mediated by TrkB receptor. Transgenic mice were subjected to saline or 1NMPP1 pretreatment, respectively. No significant difference was observed in the immobility time between saline and 1NMPP1 treated control groups. In saline group, both 7,8-DHF and 4'-DMA-7,8-DHF substantially reduced the immobility time; in contrast, neither 4'-DMA-7,8-DHF nor 7,8-DHF had any significant effect on the immobility time after 1NMPP1 treatment (FIG. 5C), suggesting that inhibition of TrkB signaling cascade blocks the antidepressant effect by the TrkB agonists. Thus, these data demonstrate that 4'-DMA-7,8-DHF and its parental lead mimic BDNF and act as potent antidepressant drugs in mice through activating TrkB receptor.

EXAMPLE 7

Imidazole Flavonoid Derivative Exhibits Strong p-TrkB Activity

Figure 6A:
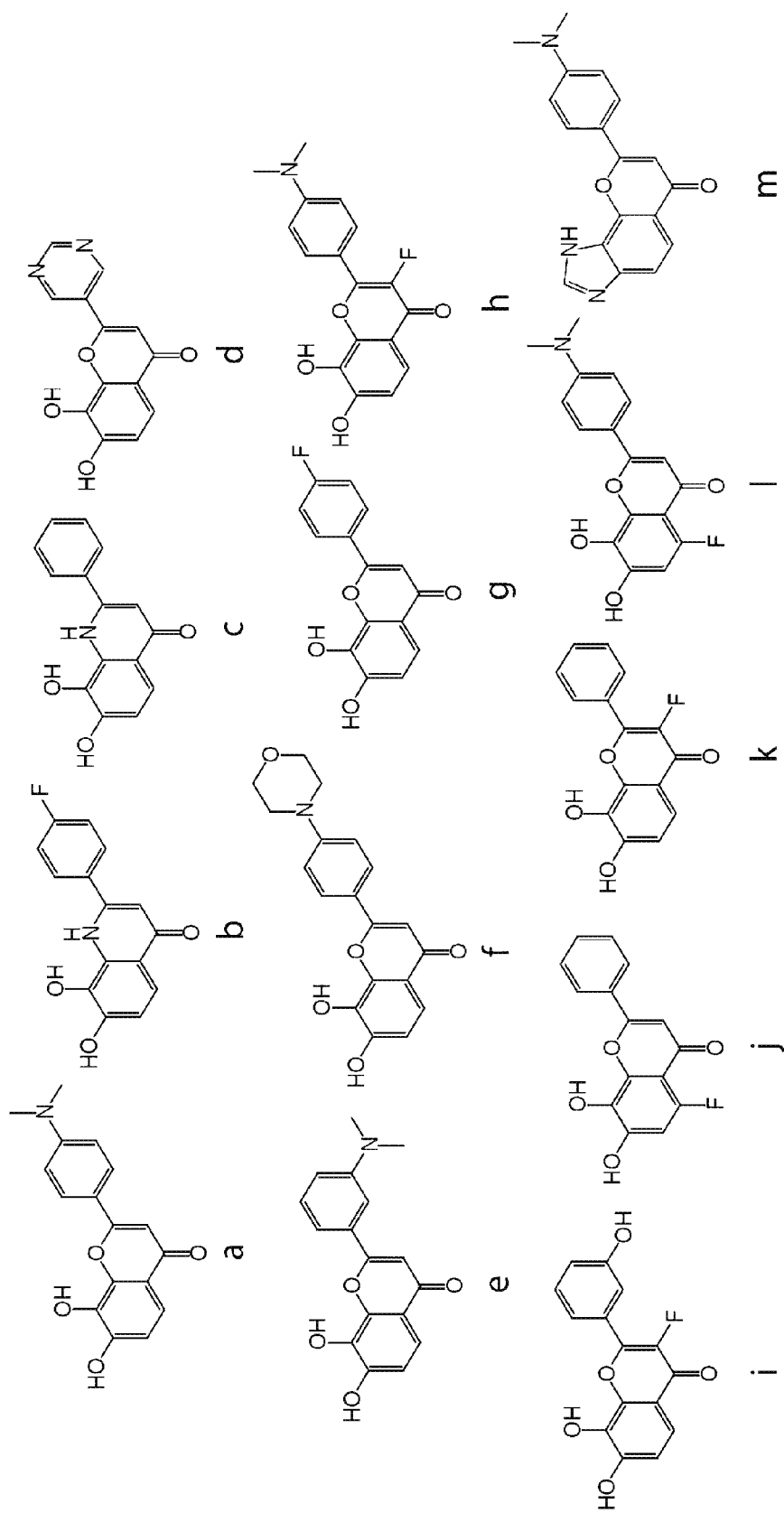
FIG. 6A illustrates 7,8-dihydroxyflavone derivatives chemical structures.
Figure 6B:
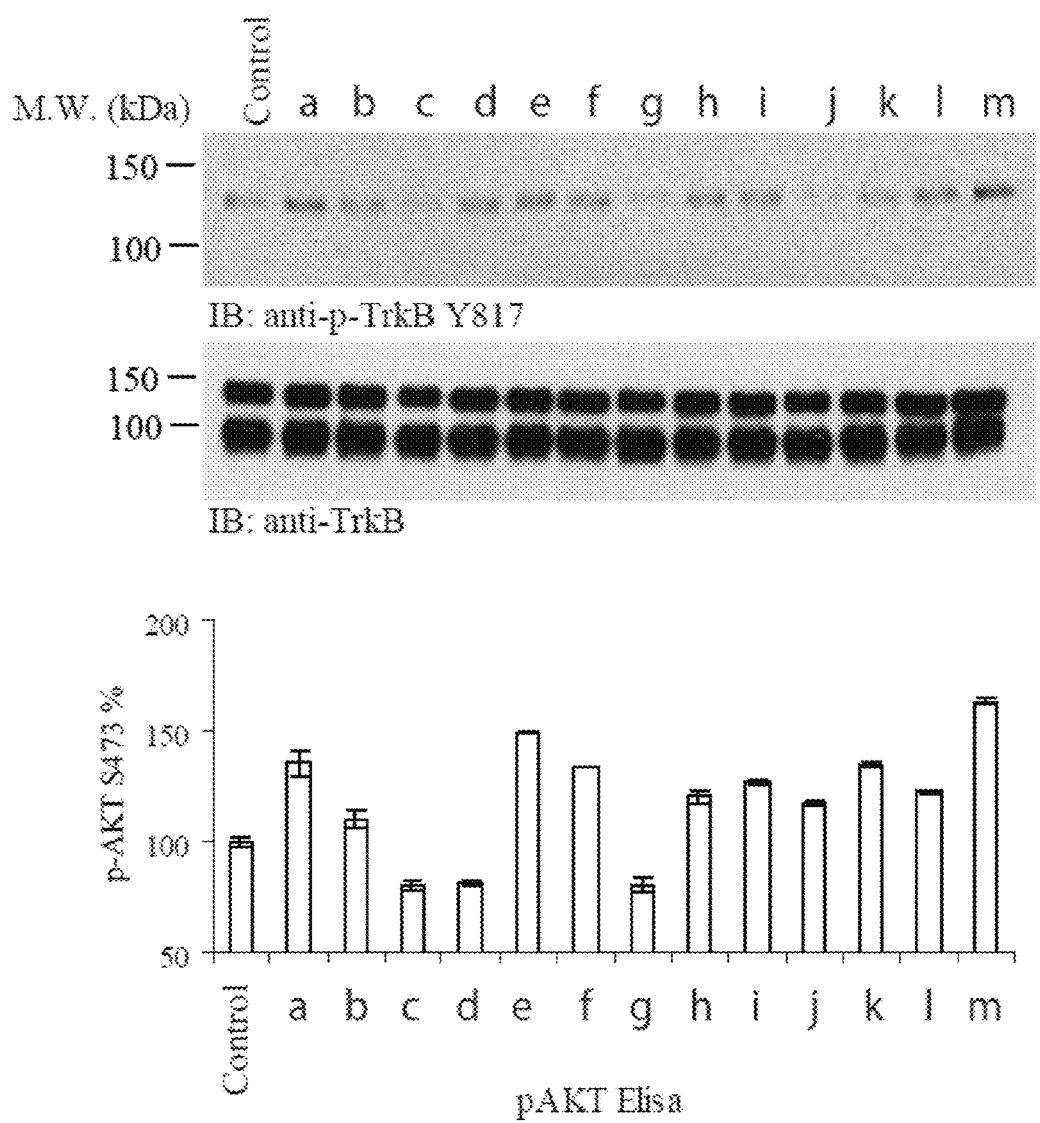
FIG. 6B shows data from immunoblotting analysis with neuronal lysates. Primary rat cortical neurons from E17 embryos (13 days in vitro (DIV)) were treated with 500 nM various chemicals for 15 min. The neuronal cell lysates were collected and resolved on 10% SDS-PAGE. Immunoblotting was conducted with various antibodies. p-TrkB Y817 antibody was employed at 1:20,000-40,000 dilution (top panel). Equal amount of TrkB was loaded in all of the samples (middle panel). P-Akt 473 ELISA analysis with the neuronal lysates (bottom panel).
Figure 6C:
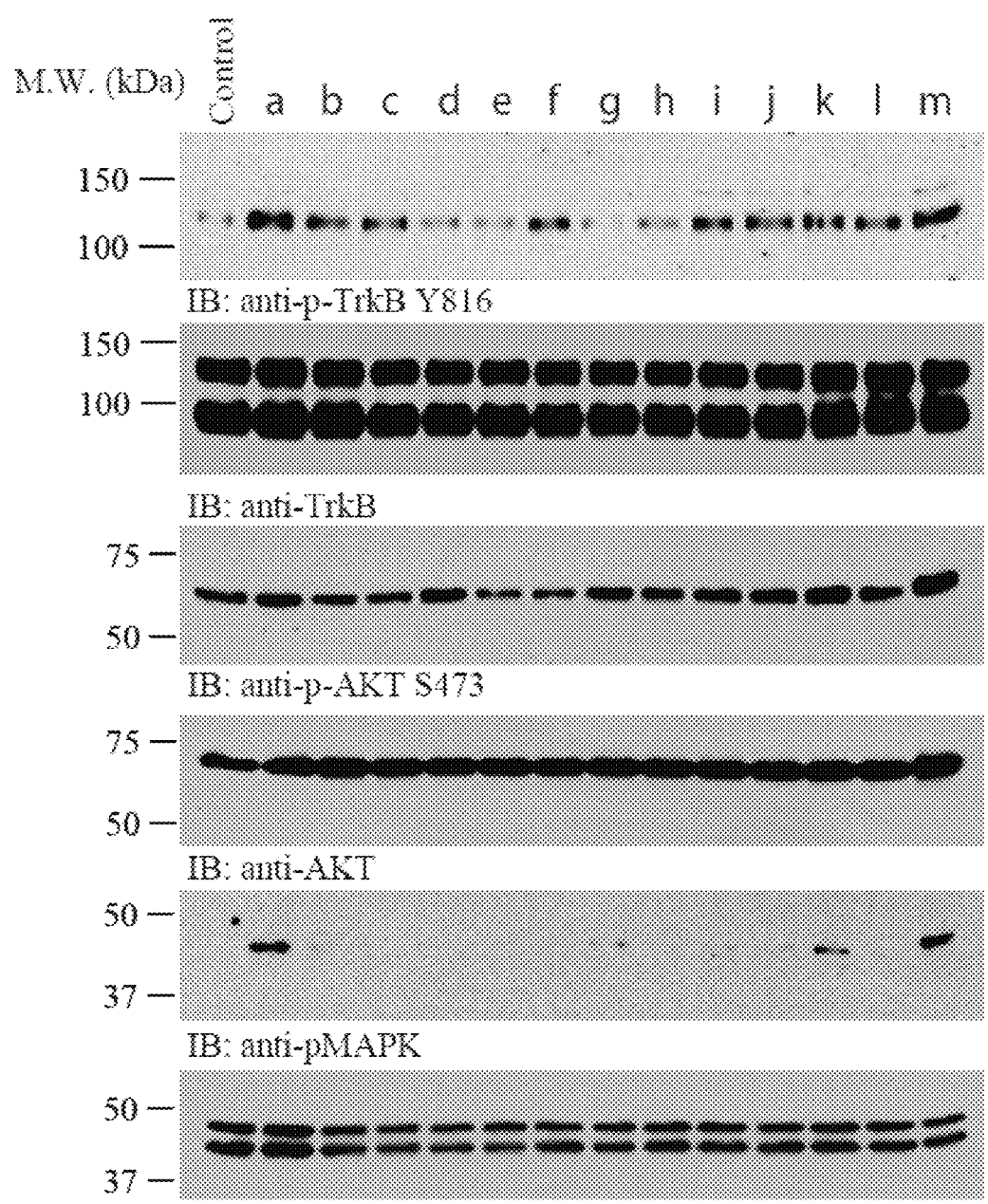
FIG. 6C shows data from immunoblotting analysis of p-TrkB and its downstream signaling with mouse brain tissues. 1 mg/kg of various compounds were orally administrated into C57 BL/6J mice and TrkB phosphorylation and its downstream signaling cascades including Akt and MAPK in mouse brain were analyzed by immunoblotting at 2 h. Akt and MAPK activation by immunoblotting with p-Akt 473 and p-MAPK antibodies verified that both 4'-dimethylamino-7,8-DHF and imidazole-flavonoid potently activated TrkB signaling in mouse brain.
Figure 7A:
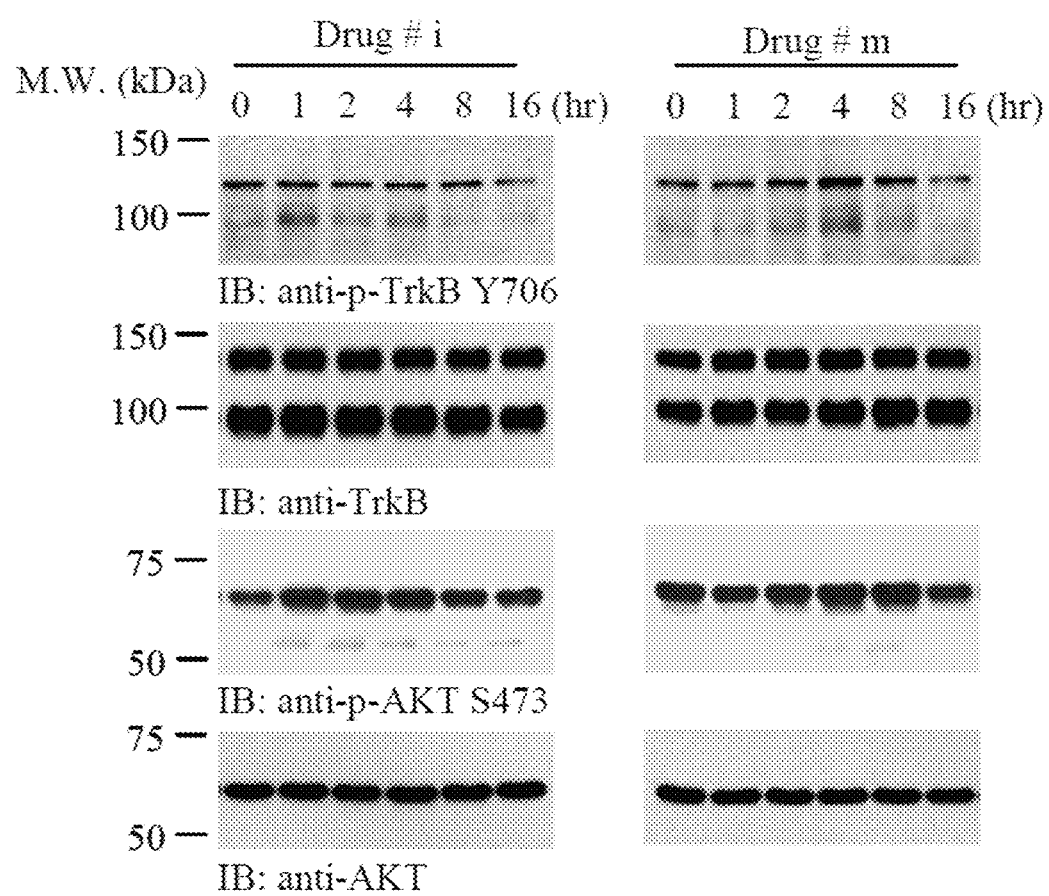
FIG. 7A shows data on signaling cascades in the mouse brain. Time course assay with compound i and m in mouse brain. 1 mg/kg of compound i and m were orally administrated into C57 BL/6J mice and TrkB phosphorylation and its downstream signaling cascades including Akt and MAPK in mouse brain were analyzed by immunoblotting at various time points. Imidazole flavonoid triggered more robust and sustained TrkB activation than compound i.
Figure 7B:
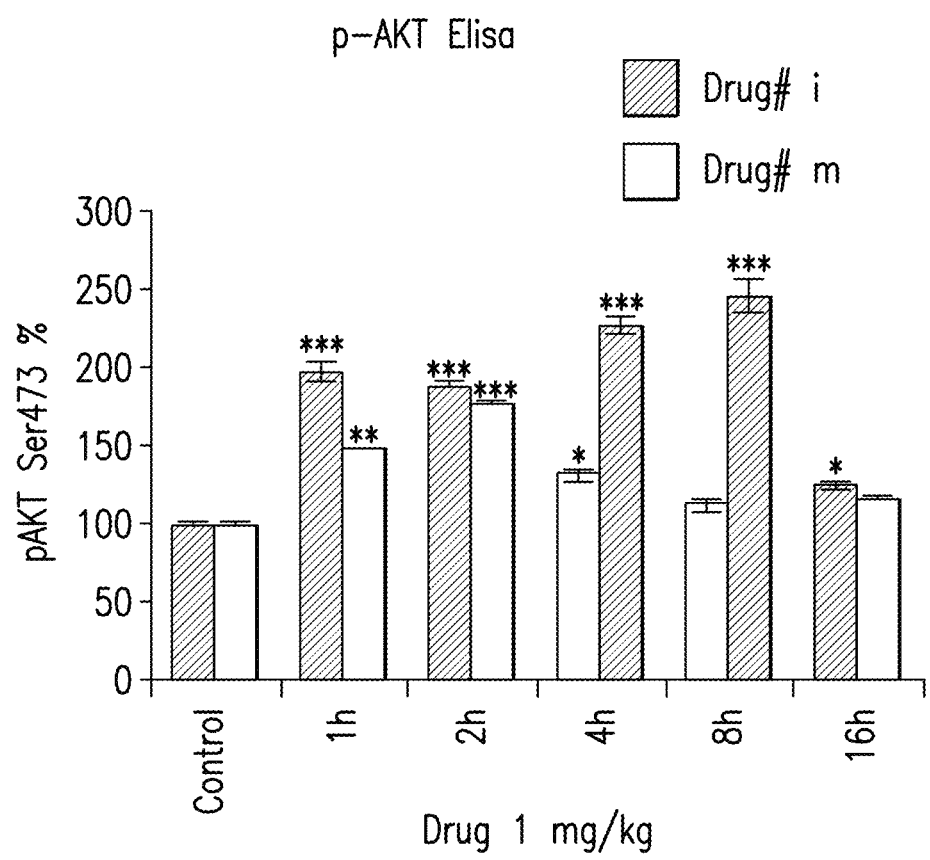
FIG. 7B shows data from a p-Akt ELISA assay with the mouse brain tissues. The brain lysates were prepared and analyzed with p-Akt ELISA kit. Imidazole flavonoid elicited more robust and sustained Akt activation than compound i.

Additional compounds are listed as designated from a to m (FIG. 6A). The compounds were dissolved in DMSO, then diluted into 500 μM with 1× PBS (final vehicle contains 10% DMSO/PBS). The primary rat cortical neurons (13 DIV) were treated with 500 nM compounds for 20 min. The cell lysates were analyzed by immunoblotting. 4'-Dimethylamino-7,8-dihydroxyflavone (compound a) activated TrkB better than compounds b to d (FIG. 6B, top panel lane 2-5). Compound, the imidazole flavonoid derivative (compound m) exhibited strong p-TrkB activity (FIG. 6C, top panel, last lane). Moreover, p-Akt ELISA was monitored to quantitatively analyze the agonistic activities of these compounds. P-Akt activities correlated with p-TrkB patterns (FIG. 6C, bottom panel panel), suggesting the imidazole derivative possesses the strongest effect in activating TrkB receptor.

The compounds were orally injected (1 mg/kg) into C57BL/6J mice. The TrkB and its downstream signaling cascades activation at 2 h were examined after drug administration with mouse brain tissues. Among these compounds, compound a and m exhibited the strongest TrkB phosphorylation. The downstream p-Akt and p-MAPK tightly coupled to p-TrkB signals. Together, this data suggests that the catechol group (7,8-dihydroxy in A ring) might be replaced with imidazole ring.

EXAMPLE 8

Imidazole-flavone Demonstrates Antidepressant Effect in Forced Swim Test Model

Figure 8A:
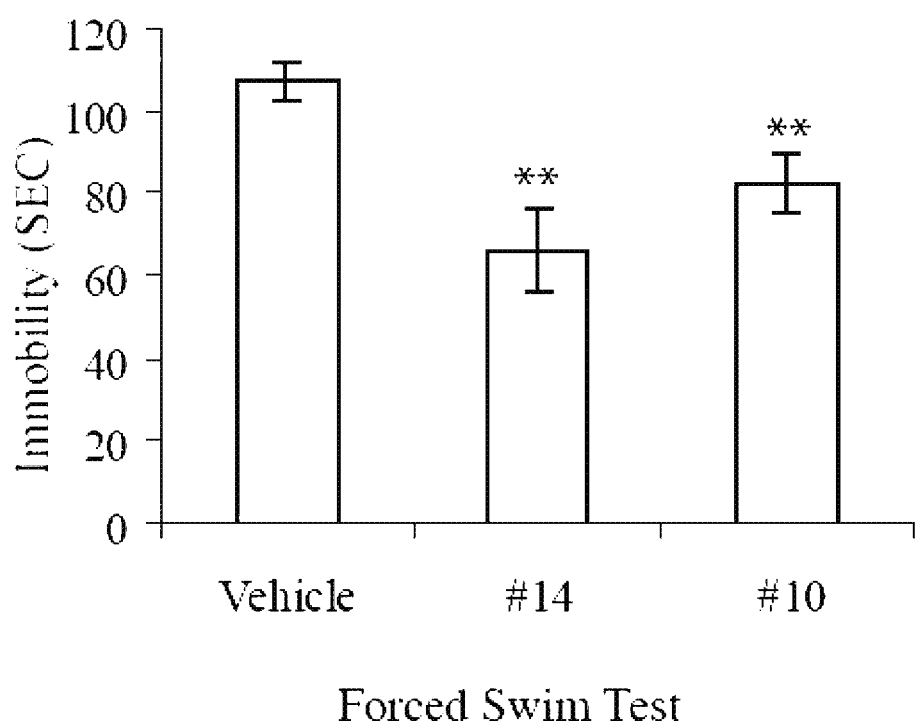
FIG. 8A shows data suggesting that imidazole-flavonoid (compound m) demonstrates robust antidepressant effect. Forced swim test with imidazole flavonoid and compound i. Male C57BL/6J mice (8 mice/group) were orally administrated by gavage with 5 mg/kg 4'-DMA-7,8-DHF and 7,8-DHF and vehicle solvent saline for 21 days, and subjected to a forced swim test (6 min, immobility recorded in the last 4 min). Data are presented as mean±SEM. Analysis of variance (ANOVA) revealed significant difference between vehicle and either compound i or compound m (n=6, ***P<0.0001 against vehicle).
Figure 8B:
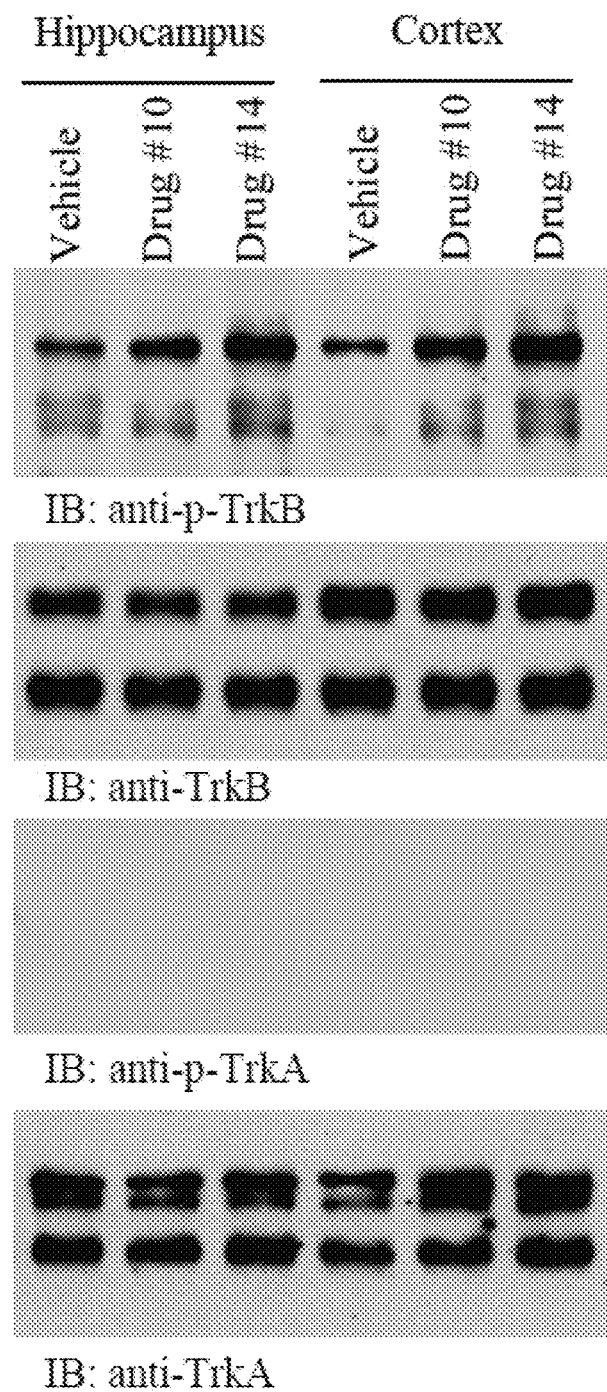
FIG. 8B shows data indicating TrkB but not TrkA is activated by both compound m and i in mouse brain. The brain lysates from above chronically treated mice were analyzed by immunoblotting with anti-p-TrkA 794 and p-TrkB 817.

BDNF/TrkB signaling plays an role in mediating antidepressants' therapeutic effects. A forced swim test is broadly used for screening of potential antidepressant drugs and is widely used to measure antidepressant activity. To explore whether imidazole flavanoid and compound i have any antidepressant effect like BDNF, a forced swim test was conducted after chronic treatment of the mice for 21 days via oral administration. When mice were treated with both compounds (5 mg/kg), the swimming immobility was significantly decreased. Notably, imidazole-derivative displayed a more robust antidepressant effect than compound i (FIG. 8A). Immunoblotting analysis revealed that both compounds evidently provoked TrkB but not TrkA activation in mouse brain with imidazole-derivative showing stronger activity than compound i (FIG. 8B). These data from chronic treatment mice are consistent with the findings that imidazole flavanoid exhibits more potent stimulatory effect on TrkB receptor in primary cultures and in mouse brain.

The invention claimed is:
1. A method of treating of treating depression comprising administering, to a subject in need thereof, an effective amount of a compound Formula F,

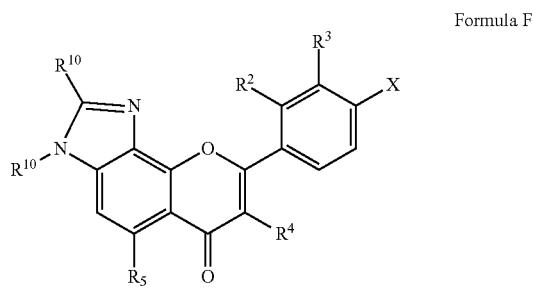

Formula F or salts or prodrugs thereof wherein,
X is hydrogen, dialkylamino, or heterocyclyl, wherein X is optionally substituted with one or more, the same or different $R^8$;
$R^2$ is hydrogen, alkoxy, hydroxy, or alkanoyloxy, wherein $R^2$ is optionally substituted with one or more, the same or different $R^8$;
$R^3$ is hydrogen, alkoxy, hydroxy, dialkylamino, or alkanoyloxy, wherein $R^3$ is optionally substituted with one or more, the same or different $R^8$;
$R^4$ is hydrogen or halogen;
$R^5$ is hydrogen, alkoxy, hydroxy, or alkanoyloxy wherein $R^5$ is optionally substituted with one or more, the same or different $R^8$; and
$R^8$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^8$ is optionally substituted with one or more, the same or different, $R^9$;
$R^9$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl; and
$R^{10}$ and $R^{11}$ are each, the same or different hydrogen, alkyl, or alkanoyl.
2. The method of claim 1, wherein the compound is selected from:
8-(4-(dimethylamino)phenyl)chromeno[7,8-d]imidazol-6 (3H)-one and
8-(4-(dimethylamino)phenyl)-7-fluorochromeno[7,8-d] imidazol-6(3H)-one, or salts thereof.
3. The method of claim 1, wherein the composition is administered in combination with an antidepressant.

* * * * *